United States Patent [19]
Kato et al.

[11] Patent Number: 5,948,659
[45] Date of Patent: Sep. 7, 1999

[54] RECOMBINANT FRUCTOSYL AMINO ACID OXIDASE

[75] Inventors: Nobuo Kato, Kameoka; Yasuyoshi Sakai, Otsu; Yoshiki Tani; Hiroshi Fukuya, both of Kyoto, all of Japan

[73] Assignee: Kyoto Daiichi Kagaku Co., Ltd., Kyoto-fu, Japan

[21] Appl. No.: 09/031,059

[22] Filed: Feb. 26, 1998

Related U.S. Application Data

[62] Division of application No. 08/899,172, Jul. 23, 1997.

[30] Foreign Application Priority Data

Jul. 23, 1996 [JP] Japan .................................. 8-193344

[51] Int. Cl.$^6$ .............................. C12N 9/02; C07H 21/04
[52] U.S. Cl. ................. 435/189; 435/252.3; 435/252.33; 435/254.11; 435/254.3; 435/320.1; 435/191; 536/23.2; 536/23.1; 536/23.7; 536/23.74
[58] Field of Search .................................. 435/189, 252.3, 435/252.33, 254.11, 254.3, 320.1, 191; 536/23.1, 23.2, 23.7, 23.74

[56] References Cited

PUBLICATIONS

Yoshida et al. Primary structure of fungal fructosyl amino oxidases and their application to the measurement of glycated proteins Eurp. J. Biochem. 242, 499–505, Dec. 15, 1996.

Yoshida et al, "Distribution and properties of fructosyl amino acid oxidase in fungi" Appl. Environ. Microbiol. 61(12), 4487–4489, Dec. 1995.

Takahashi et al. "Molecular cloning and expression of Amadoriase isoenzyme . . . " J. Biol. Chem. 272, 12505–12507, May 9, 1997.

*Primary Examiner*—Robert A. Wax
*Assistant Examiner*—Nashaat T. Nashed
*Attorney, Agent, or Firm*—Birch, Stewart, Kolasch & Birch, LLP

[57] ABSTRACT

The present invention provides a recombinant protein which shows fructosyl amino acid oxidase activity, a DNA encoding the same, an expression vector containing the DNA, a transformant transformed by the expression vector, and the method of preparing recombinant fructosyl amino acid oxidase by culturing the resultant transformant, and the recombinant fructosyl amino acid oxidase thus obtained.

5 Claims, 10 Drawing Sheets

ProValThrLysSerSerSerIleLeuIleIleGlyAlaGlyThrTrpGly
CCNGTNACNAARWSNWSNWSNATHYTNATHATHGGNGCNGGNACNTGGGN
                        ――――――――――――――――――――――――――――
                                                 Primer 1

LeuThrArgProGluGlnPheArgGlnLeuAlaProGlyValLeuLys
YTNACNMGNCCNGARCARTTYMGNCARYTNGCNCCNGGNGTNYTNAAR
―――――――――――――――――――――――――――――――――――――――――――――――
                        Primer 2

Lane A : *C. boidinii* TK62/pNEL14 strain
Lane B : TK62/pNEL11 strain
Lane C : TK62/pNEL1 strain
Lane D : S2 AOU-1

RECOMBINANT FRUCTOSYL AMINO ACID OXIDASE

This application is a divisional of copending application Ser. No. 08/899,172, filed on Jul. 23, 1997, the entire contents of which are hereby incorporated by reference.

FIELD OF THE INVENTION

The present invention relates to a production of recombinant protein having an enzymic activity of fructosyl amino acid oxidase. More particularly, it relates to a DNA encoding fructosyl amino acid oxidase derived from microorganism, an expression vector containing the DNA which is functional in a host cell, a transformant transformed by the expression vector, and the method of preparing recombinant fructosyl amino acid oxidase by culturing the resultant transformant, and the recombinant fructosyl amino acid oxidase thus obtained.

BACKGROUND OF THE INVENTION

When reactive substances such as protein, peptide and amino acid having an amino group(s) coexist with a reducing sugar such as aldose having an aldehyde group(s), they combine nonenzymatically and irreversibly through the amino and aldehyde groups, which is followed by amadori rearrangement to form an amadori compound. Examples of materials containing an amadori compound include food products such as soy sauce and body fluids such as blood. The production rate of an amadori compound being a function of concentration of reactants, contacting period, temperature and the like, various useful information about a sample containing such a reactive substance(s) can be derived from the amount of amadori compounds.

For instance, fructosylamines which are amadori compounds wherein glucose is bound to amino acid residue are formed in a living body. The so produced glycated derivatives of hemoglobin, albumin and proteins in blood are called glycohemoglobin, glycoalbumin and fructosamine, respectively. As the concentration of these glycated derivatives in blood reflects an average of blood sugar levels over a particular period of time, it can be used as a significant index for diagnosis and control of conditions of diabetes. Therefore, the establishment of a method of measuring an amadori compound in blood is clinically useful.

Further, a state of preservation and period after production of a food product can be estimated on the basis of the amount of amadori compounds in the food product. Accordingly, the method of measuring an amadori compound can also contribute to the quality control of a food product.

Thus, an assay of amadori compounds should be useful in wide range of fields involving medicine and food products.

There has been proposed an assay of amadori compounds which comprise reacting an oxidoreductase with a sample suspected to contain amadori compounds and determining oxygen consumption or hydrogen peroxide generation as an index of the amount of amadori compounds.

The decomposition of amadori compounds catalyzed by an oxidoreductase can be represented by the following reaction scheme:

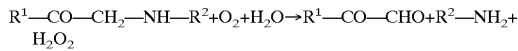

wherein $R^1$ is an aldose residue and $R^2$ is an amino acid, protein or peptide residue.

The enzymatic assay of amadori compounds and enzymes usable therefor are well known in the art from literatures, such as Japanese Patent Publication (KOKOKU) No. 5-3399, Japanese Patent Publication (KOKAI) Nos. 61-268178, 2-195900, 3-155780 and 2-195899.

However, the existing assays and the enzymes are not necessarily useful for a particular purpose. It is needed to select the most suitable enzyme for individual purpose so as to perform the determination of an amadori compound correctly and efficiently. For example, the glycoalbumin level reflects the mean glycoprotein value of for past 1 to 2 weeks and it is desirable to use an enzyme with higher substrate specificity to fructosyl valine than fructosyl lysine in glycated protein in blood for the diagnosis of diabetes. However, such an enzyme has not been provided so far. The above-mentioned Japanese Patent Publication (KOKAI) 3-155780 discloses an enzyme from Aspergillus having molecular weight of about 80,000 to 83,000, but the enzyme is less active on fructosyl lysine compared to fructosyl valine.

On the other hand, an enzyme active on both of fructosyl valine and fructosyl lysine is preferred for the determination of glycated hemoglobin.

The present inventors have intensively studied for purposes of providing an enzyme useful for establishing the purposes above, and have purified a fructosyl amino acid oxidase (FAOD) from Fusarium and disclosed the usefulness thereof (Japanese Patent Publication (KOKAI) 8-154672 corresponding to EP-A-709457); Japanese Patent Publication (KOKAI) 7-289253 corresponding to EP-A-678576), and from Aspergillus (PCT/JP96/03515). The inventors have found that these FAODs contain an enzyme which is more specific to fructosyl lysine than fructosyl valine, for example, the one produced by *Aspergillus terreus* GP1 (FERM BP-5684), and named the enzyme of this kind "FAOD-L". As the FAOD-L was expected to be useful for diagnosis of diabetes, the present inventors have continued research on it.

However, it requires a plenty of labor and time to grow a microorganism such as a strain of Aspergillus in a medium and purify an enzyme from the culture, and is inefficient. In addition, an enzyme isolated from the culture is probably accompanied with contaminants such as proteins originated from the strain of Aspergillus, which can contain a substance capable of affecting the FAOD activity reversely, and would reduce the reliability of assay.

A purified FAOD originated from a microorganism can be obtained efficiently by means of DNA recombinant technology which comprises cloning a DNA encoding an FAOD, constructing an appropriate expression vector containing the DNA, transforming an appropriate host cells by the expression vector, and culturing the transformant in an appropriate medium. However, DNA encoding an FAOD originated from Fusarium or Aspergillus has not been cloned prior to the present invention. Accordingly, it was necessary to isolate DNA encoding an intended FAOD from a microorganism.

SUMMARY OF THE INVENTION

The present inventors have succeeded in the preparation of a recombinant protein having desired FAOD activity by cloning a DNA encoding FAOD-L from *Aspergillus terreus* GP1 FERM BP-5684, constructing an expression vector containing the DNA, transforming a host cell using the expression vector, and growing the transformant in a medium.

Accordingly, the present invention provides a recombinant protein having the amino acid sequence defined in SEQ ID No. 1 or an amino acid sequence derived from that defined in SEQ ID No. 1 through the deletion, substitution, insertion or addition of one to several amino acids, which has the fructosyl amino acid oxidase activity.

DESCRIPTION OF THE PREFERRED EMBODIMENT

Figures 1, 2:
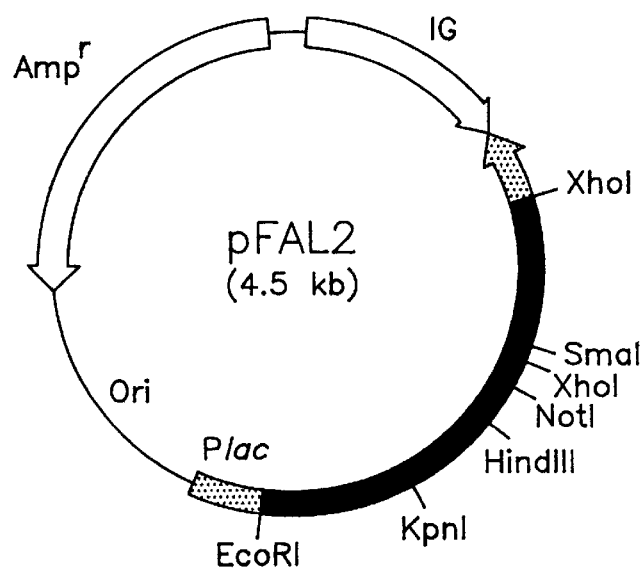
FIG. 1 shows the relationships between primers (SEQ ID NOS: 10 and 11) used in the PCR and partial amino acid sequences (SEQ ID NOS: 4 and 5) of FAOD-L purified from *A. terreus* GP1 FERM BP-5684.
FIG. 2 is a schematic restriction map of plasmid pFAL2, encoding FAOD-L to be used for transforming procaryotic host cells.

Throughout the specification, the term "a protein having the fructosyl amino acid oxidase activity or FAOD activity" or the like means that the said protein has an enzymic activity for catalyzing the reaction wherein an amadori compound is oxidized to yield α-ketoaldehyde, amine derivatives and hydrogen peroxide.

The protein of the present invention obtained through the DNA recombinant technology may be referred to as simply "FAOD-L" or "recombinant FAOD-L".

The protein of the present invention has characteristics as a recombinant product while retaining the enzymic activity of the naturally occurring FAOD-L as shown below:

1) It has an enzymic activity for catalyzing the reaction wherein an amadori compound is oxidized to yield α-ketoaldehyde, amine derivatives and hydrogen peroxide.

2) It is composed of two identical subunits with molecular weight of about 48,000 daltons (48 kDa) when estimated on SDS-PAGE.

3) It is more active on fructosyl lysine compared to fructosyl valine.

4) It is substantially free from contaminating proteins of a strain of Aspergillus As the amino acid sequence of FAOD-L and a nucleotide sequence encoding it are disclosed by the present invention, it is easy for one ordinary skilled in the art to obtain a variant which shows an activity similar to FAOD-L and has varied amino acid sequence obtainable by a conventional method, such as site-specific mutagenesis of DNA, which involves the insertion, deletion, substitution or addition of one or more amino acids, which variant has an activity similar to FAOD-L. The kind of mutation, number of amino acids and/or site to be mutated can be determined freely as far as the FAOD-L activity is retained. Accordingly, the so obtained FAOD-L variants also fall within the scope of the invention. It should be noted that the number of amino acids involved in the mutation is not critical for the present invention. Therefore, as is easily understood by one of ordinary skilled in the art, the present invention includes variants involving insertion, deletion, substitution or addition of more than several amino acids on condition that the variant is construed as falling within the scope of the invention from various points of view, such as purpose, constituent, effect and the like.

The present invention also provides a DNA encoding the recombinant protein of the present invention as defined above. The DNA can be cDNA or synthetic DNA. The DNA of the present invention has, for example, the nucleotide sequence of SEQ ID No. 2. Further, the DNA of the present invention includes a DNA capable of hybridizing with the DNA having the nucleotide sequence of SEQ ID No. 2 under a stringent condition, and encoding a protein having FAOD-L activity.

The present invention further provides an expression vector containing a DNA encoding FAOD-L as defined above. The vector of the present invention is functional in both of procaryotic and eucaryotic cells.

The term "functional" regarding the expression vector of the present invention means that the vector, when introduced into a host cell, can allow the transformant to grow on an appropriate medium and produce the FAOD-L encoded by the vector.

Further, the present invention provides a host cell transformed with the vector.

The present invention also provides a method of producing a recombinant FAOD-L by growing the transformant in an appropriate medium and recovering the expression product from the culture.

As is apparent from the above, the present invention provides a protein having FAOD-L activity characterized in that it is obtainable by a method comprising constructing an expression vector using a DNA having a nucleotide sequence shown in SEQ ID No. 2 or one capable of hybridizing with the said DNA under a stringent condition and encoding a protein having the FAOD-L activity, transforming a host cell with the expression vector, and growing the resultant transformant in a medium.

The recombinant protein of the present invention is, as shown in the Examples below, useful in an assay for determining Amadori compounds in a sample suspected to contain the same. Accordingly, it is useful in various fields in which such assay is involved. It is especially useful for diagnosing diabetes by determining glycated Amadori compounds in serum, and for determining glycated hemoglobin.

Cloning of a DNA encoding FAOD-L can be carried out in a conventional manner using any microorganism producing an FAOD-L, preferably a strain of Aspergillus terreus GP1, which has been deposited at the "National Institute of Bioscience and Human-Technology, Agency of Industrial Science and Technology", Tsukuba-shi, Ibarakiken, Japan (original deposition date: May 31, 1996; international deposition date: Sep. 30, 1996) under the accession number of FERM BP-5684.

The present inventors isolated and purified an FAOD-L from a culture of A. terreus GP1 and determined the N-terminal amino acid sequence. Internal amino acid sequence was then determined by restricted digestion of FAOD-L. The inventors designed and synthesized oligonucleotide primers based on the partial amino acid sequences. The N-terminal and internal amino acid sequences are shown in SEQ ID Nos. 3 and 4, respectively. The nucleotide sequence of oligonucleotide primers 1 and 2 are shown in SEQ ID Nos. 5 and 6, respectively. FIG. 1 shows the relationships between the peptide fragments shown in SEQ ID Nos. 3 and 4, and primers 1 and 2.

The inventors cultivated A. terreus GP1 in a GL brown-colored medium (EP-A-7-90457, EP-A-678576), isolated total RNA from the cultured cells, and purified mRNA with mRNA Purification Kit (Pharmacia). The GL-brown colored medium used to induce the FAOD-L production in A. terreus GP1 can be prepared by adding fructosyl lysine and/or $N^\alpha$-Z-lysine (FZL) to any of conventional medium, or by autoclaving a medium containing glucose together with lysine and/or FZL. The mRNA was then converted into cDNA using a reverse transcriptase, and a cDNA library was constructed using λZAPII vector in a conventional manner.

An RT-PCR (reverse transcription polymerase chain reaction) was conducted using the total RNA and primers above to obtain about 400 bp PCR product. The PCR product was subcloned to obtain a fragment, which was used as a probe in the screening of the cDNA library to give 7 positive clones. Each of cDNA fragments contained in the clones was subcloned into plasmid pBluescript II SK⁻ to obtain expression vectors. The expression vector was then transformed into Escherichia coli JM109 competent cells (Takara Shuzo). After growing transformants, one clone E. coli JM109/pFAL2 harboring plasmid pFAL2 comprising a nucleotide sequence corresponding to the N-terminal amino acid sequence of FAOD-L was selected. In a similar manner, other clone of E. coli, that is, E. coli SOLR/pFAL2 was prepared using E. coli SOLR obtained from RETRIEVAL OF TOXIC CLONES (STRATAGENE).

The base (nucleotide) sequence of the resultant clone was determined and the amino acid sequence of FAOD-L was deduced therefrom. The amino acid and base sequences are shown in SEQ ID Nos. 1 and 2, respectively. One of transformants, E. coli SOLR/pFAL2, has been deposited at the "National Institute of Bioscience and Human-Technology, Agency of Industrial Science and Technology", Tsukuba-shi, Ibaraki-ken, Japan under the accession number of FERM BP-5981 since Jun. 16, 1997.

The pFAL2 of the present invention is an expression vector replicable in an E. coli host cells, and contains lac promoter, SD sequence and a DNA sequence encoding resistance against ampicillin. As is recognized by one ordinary skilled in the art, any expression vectors capable of allowing the expression of FAOD-L in different host cells can be constructed just by isolating the DNA fragment encoding FAOD-L contained in pFAL2 of the present invention and inserting the fragment into an appropriate expression vector in a conventional manner.

Any cultured cells can be used as a host cell which is transformed by the expression vector harboring the DNA encoding FAOD-L of the present invention. Examples of host cells include procaryotic cells such as Escherichia coli, eucaryotic cells such as yeast and cells of higher animals which are generally available. Specifically, microorganisms including procaryotic microorganisms such as bacteria (E. coli, B. subtilis, etc.), eucaryotic microorganisms such as yeast, animal cells and cultured plant cells are usable. Preferred examples of microorganisms include a strain of genus Escherichia (e.g., E. coli), yeast especially a strain of genus Saccharomyces (e.g., S. cerevisiae), a strain of genus Candida (e.g., C. boidinii). The most preferred microorganism host cell is methanol yeast (methylotrophic yeast or methanol-utilizing yeast). Preferred examples of animal cells include mouse L929 cell, chinese hamster ovary (CHO) cell and the like. In general, there are two types of expression system, i.e., intracellular- and extracellular (secreting) expression systems. For example, an expression vector capable of directing a yeast host cell to secrete the expression product can be constructed by ligating a gene encoding signal sequence of a secretor protein originated from yeast host cell to the N-terminus of a DNA encoding FAOD-L, which allows the expression product to be secreted into periplasm.

Appropriate expression vectors for transforming procaryotic cells especially E. coli host cells are known in the art. Examples of such expression vectors include those having a conventional promotor such as lac promoter, tac promotor or the like.

Appropriate expression vectors for transforming eucaryotic cells are also known in the art and one can select a suitable expression vector among them. For the expression of FAOD-L in yeast cells, expression vectors having a promotor such as GAL promotor, AOD promotor or the like, and for the expression in mammalian calls, those having a promotor such as SV40 promotor or the like are preferable. An expression vector of multi-copy type can be obtained to improve the expression efficiency by the use of a known plasmid of multi-copy type.

From the viewpoint of operability and availability, a procaryotic host cell, in particular E. coli, is preferred. However, a eucaryotic host cell, in particular yeast, is preferred to avoid the formation of inclusion bodies.

Host-vector systems are well known in the art and described in may literatures such as Maniatis, T. et al, Molecular Cloning, A LABORATORY MANUAL, Cold Spring Harbor Laboratory Press. Some host-vector systems for the FAOD-L of the present invention will be described below briefly.

For instance, an expression vector for E. coli host cells can be constructed by inserting a DNA encoding FAOD-L into a suitable expression vector at an appropriate site of the vector, downstream from a promoter. As previously mentioned, there are two types of expressions wherein the expression product is accumulated intracellularly or secreted from the cells. In the case of E. coli, the product is generally accumulated within the cells. However, an expression vector capable of directing E. coli host cells to secrete the expression product can be constructed by ligating a gene encoding signal sequence of a secretor protein originated from E. coli to the N-terminus of the DNA encoding FAOD-L, which makes the expression product to be secreted into periplasm. Similarly, there are suitable expression systems for eucaryotic host cells, wherein the expression product is accumulated within the cells or secreted into medium. For example, an expression vector capable of directing yeast host cells to secrete the expression product can be constructed by ligating a gene encoding signal sequence of a secretor protein originated from yeast to the N-terminus of the DNA encoding FAOD-L, which makes the expression product to be secreted into periplasm.

As mentioned above, the another problem for establishing an efficient expression is the formation of inclusion body. FAOD-L is originated from an eucaryotic microorganism, i.e., A. terreus GP1 FERM BP-5684, and therefore inclusion bodies are possibly formed when the protein is expressed in a procaryotic host cells, which lowers the efficiency of production. This is well known phenomenon in the art and described in the literature such as Labomanual, Gene Technology, Suppl., pp. 187, Maruzen & Co. The problem can be solved by constructing an expression vector functional in eucaryotic host cells, transforming eucaryotic host cells with the vector and allow the resultant transformants to produce FAOD-L.

Such vectors can be constructed by inserting a DNA fragment encoding FAOD-L isolated from a transformant E. coli SOLR/pFAL2 or E. coli JM109/pFAL2 described in Examples below in a conventional manner.

The construction of an expression vector for yeast is hereinafter described. However, it is only for illustration purposes and the present invention is by no means restricted to the use of the vector below.

An FAOD-L expression vector for expression of FAOD-L in yeast has been constructed using plasmid pNOTel (Japanese Patent publication (KOKAI) 5-344895; EP-0558024) which is an expression vector for integrating a DNA into chromosome. The plasmid pNOTel contains AOD promoter and URA3 gene, thereby providing a means for selecting a transformant transformed with the said plasmid on the basis of Ura-requirement.

Figure 8:
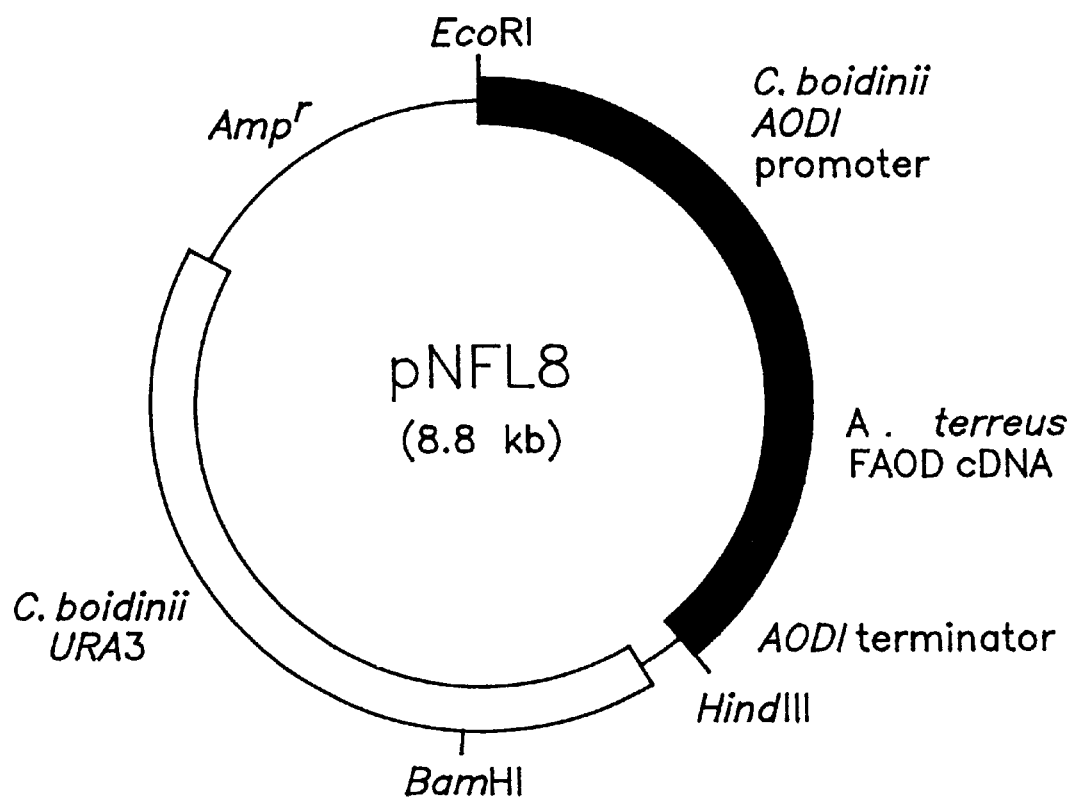
FIG. 8 is a schematic restriction map of an expression vector pNFL8 to be used for transforming eucaryotic host cells.

First, an E. coli expression vector pFAL2 containing cloned FAOD-L cDNA was isolated from E. coli SOLR/pFAL2 or E. coli JM109/pFAL2 and used as an template in the PCR wherein the primers shown in SEQ. ID. Nos. 7 and 8 each corresponding to the N-terminal and C-terminal regions of FAOD-L, respectively, followed by the purification of FAOD-L cDNA fragment of about 1.3 kb. The plasmid pNOTel was digested with restriction enzyme Not I, dephosphorylated with bovine intestine phosphatase, and blunt-ended together with the FAOD-L cDNA fragment above by the use of a DNA Ligation Kit (Takara Shuzo, & Co.). These fragments are then ligated with the DNA Ligation Kit (Takara Shuzo, & Co.) to obtain plasmid PNFL. The plasmid PNFL was then used for transforming E. coli in accordance with the Hanahan method (Hanahan, D., Techniques for Transformation of E. coli, In: DNA Cloning, vol. I, Glover, D. M. (ed.), pp. 109–136, IRL Press, 1985). Plasmids were prepared from 84 transformants randomly selected from the resultant transformants and restricted with the restriction enzyme HindIII to determine the orientation of the insert. As a result, plasmid pNFL8 was obtained, wherein the FAOD-L cDNA fragment is inserted downstream from the AOD promoter. FIG. 8 depicts the schematic restriction map of plasmid pNFL8.

The plasmid pNFL8 was used for transforming C. boidinii TK62 which is an Ura-requiring strain and the resultant transformant was grown in YNB medium lacking Ura. From the URA$^+$ trasformants, 14 strains were selected randomly and grown in a basal medium containing methanol. As is shown in Table 3 below, 11 strains produced FAOD-L. Southern analysis of the transformants revealed that most transformants contain single copy.

In the description above, certain examples of expression vectors and host cells suited for the expression of a DNA encoding FAOD-L are shown. It is possible for one ordinary skilled in the art to construct an expression vector functional in an host cell by using a promoter selected from those known in the art or newly prepared one.

Thus, the present invention is by no means to be restricted to the expression vectors shown in the present specification but includes those obtainable through the modification, e.g., changing the promoter, according to a conventional manner which are functional in different microorganisms or cells and/or can make the host cells produce FAOD-L to higher level.

Transformation of host cells with an expression vector can be carried out in a conventional manner such as the method described in the Molecular Cloning, A LABORATORY MANUAL, Cold Spring Harbor Laboratory Press. It can be done by the competent cell or electroporation method, in the case of procaryotic or eucaryotic cells, and the transfection or electroporation method in the case of mammalian cells. The resultant transformants are cultured in an appropriate medium.

The medium usable for the production of FAOD-L of the present invention can contain a carbon source (e.g., glucose, methanol, galactose, fructose, etc.) and inorganic or organic nitrogen source (e.g., ammonium sulfate, ammonium chloride, sodium sulfate, peptone, casamino acid, etc.). Other nutrients such as inorganic salts (e.g., sodium chloride, potassium chloride), vitamins (e.g., vitamin $B_2$), antibiotics (e.g., ampicillin, tetracycline, kanamycin) can be optionally added to the medium. For mammal cells, Eagle's medium is preferred.

When the host cell is a methanol yeast, a basal medium containing 0.1 to 5.0%, preferably 0.5 to 2.0% $NH_4Cl$ and/or 0.1 to 5.0%, preferably 1% yeast extract, and 0.1 to 5.0%, preferably 1.5% methanol is preferred. As is shown in Tables 4 and 5 below, which show the production of FAOD-L by methanol yeast under various cultivating conditions, FAOD-L can be produced in a basal medium containing 1.5% methanol. However, the production can be improved when the medium contains $NH_4Cl$ as the carbon source and yeast extract at a concentration of about 1%.

The cultivation of transformants is normally conducted at temperature range of 25 to 40° C., preferably at 30 to 37° C. in a medium of pH range of 6.0 to 8.0, preferably 7.0 for 8 to 48 hr in the case of procaryotic host cells; and at temperature range of 25 to 40° C., preferably at 28° C. in a medium of pH range of 5.0 to 8.0, preferably 5.5 to 6.0 for 16 to 96 hr in the case of eucaryotic host cells.

When the produced FAOD-L is continued in the medium or supernatant of the medium, the cultured medium is filtered or centrifuged to obtain the supernatant. The purification of FAOD-L from the supernatant can be carried out in a conventional manner commonly used for the isolation and purification of a naturally occurring or synthetic proteins, for example, dialysis, gel-filtration, affinity column chromatography using anti-FAOD-L monoclonal antibody, column chromatography using an appropriate adsorbent, high performance liquid chromatography and the like. When the produced FAOD-L is contained in the periplasm or cytoplasm of transformants, the cells are harvested by filtration or centrifugation and ground by, for example, ultrasonic treatment and/or lysozyme treatment to destroy the cell walls and/or cell membranes to obtain cell debris. The cell debris is then dissolved in an appropriate aqueous solution such as Tris-HCl buffer. FAOD-L can be purified from the so obtained solution in accordance with a conventional method.

Re-folding of the FAOD-L produced by a transformant can be conducted in a conventional manner, if necessary.

Although the culture obtained by growing a transformant of the present invention in an appropriate medium has FAOD-L activity as it is, it can be treated by a method known to one ordinary skilled in the art to obtain a processed material such as enzyme solution or the like. It can be purified in a manner similar to those described above, if necessary, which comprise, for example, collecting transformants producing FAOD-L by centrifugation, suspending the cells into a phosphate buffer, grinding cells by ultrasonic treatment, and centrifuging the suspension to obtain an enzyme preparation. Purified enzyme can be obtained by applying the supernatant to dialysis followed by chromatography. The purified enzyme is further treated by an enzyme such as restriction enzyme or exonuclease to obtain a fragment having FAOD-L activity, if necessary. The fragment obtained in such a manner is also useful for purposes of the present invention and falls within the scope of the invention.

As mentioned above, the product obtained by culturing the transformant or a processed material thereof has a catalytic activity in the reaction represented by the scheme:

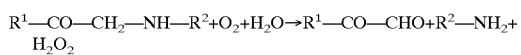

wherein $R^1$ is an aldose residue and $R^2$ is an amino acid, protein or peptide residue.

In the above reaction scheme, Amadori compounds of the formula $R^1$—CO—$CH_2$—NH—$R^2$ wherein $R^1$ is —OH, —$(CH_2)_n$— or —$[CH(OH)]_n$—$CH_2OH$ (n is an integer of 0 to 6) and $R^2$ is —$CHR^3$—$[CONHR^3]_m$COOH ($R^3$ is a side chain residue of an α-amino acid and m is an integer of 1 to 480) are preferred as a substrate. Among them, compounds wherein $R^3$ is a side chain residue of an amino acid selected from lysine, polylysine, valine, asparagine, etc., n is 5 to 6 and m is 55 or less are more preferred.

The assay of Amadori compound using the FAOD-L of the present invention is carried out in a conventional manner by bringing the sample containing an Amadori compound into contact with FAOD-L of the present invention in an aqueous solution or a buffer, and determining the amount of oxygen consumed or that of hydrogen peroxide produced. The assay can be carried out, for example, on the basis of the measurement of the amount of glycated protein and/or glycation rate or the determination of fructosyl amine in a sample derived from living body.

To carry out the determination, a suspension or a solution of FAOD-L in water or a buffer is added to a solution of a sample containing Amadori compound in a buffer. The reaction conditions such as pH and temperature of the reaction mixture are not critical and can be determined on the basis of those used in a similar enzymic reactions. However, the reaction could be carried out at pH range of about 4.0–12.0, preferably about 7.0–9.0, more preferably about 8.0; and at temperature range of 25–50° C., preferably 25–40° C., more preferably 35° C. The FAOD-L of the present invention is usable in the assay for determining Amadori compound in a sample solution containing an Amadori compound. Examples of sample include those derived from food products such as soy sauce, etc. and those derived from a living body such as blood (e.g. whole blood, plasma or serum), urine, or the like.

Example of a buffer usable in the assay includes Tris-HCl buffer. The amount of FAOD-L to be used in the assay is normally 0.1 unit/ml or more, preferably 1 to 100 units/ml in the case of the end point method.

Examples of assay to which the FAOD-L of the present invention applicable are shown below, although they are not restrictive.

(1) Determination based on the amount of hydrogen peroxide generated

The amount of Amadori compounds in a sample can be estimated by obtaining a calibration curve showing the relation between the amount of Amadori compound and that of hydrogen peroxide produced, measuring the amount of hydrogen peroxide generated in a reaction mixture containing a sample to be assayed, and estimating the amount of Amadori compound in the sample by referring to the said calibration curve. The generation of hydrogen peroxide can be determined, for example, calorimetrically or by the use of hydrogen peroxide electrode. Specifically, the determination procedures are similar to those described in "Titration of FAOD-L Activity" below, wherein a reaction mixture contains 1 unit/ml FAOD-L and a diluted solution of test sample, and the amount of hydrogen peroxide produced is measured.

Examples of color-developing system usable in the assay include combinations such as 4-aminoantipyrine/N-ethyl-N-(2-hydroxy-3-sulfopropyl)-m-toluidine, 4-aminoantipyrine/N,N-dimethylaniline, 4-aminoantipyrine/N,N-diethylaniline, MBTH//N,N-dimethylaniline, 4-aminoantipyrine/2,4-dichlorophenol, and the like in the place of 4-aminoantipyrine/phenol which is used in the method (1), A in "Titration of FAOD-L Activity" below.

(2) Determination on the basis of the amount of oxygen consumed

Amadori compound in a sample can be estimated by obtaining a calibration curve showing the relation between the amount of amadori compound and that of oxygen consumed, calculating the amount of oxygen consumed in a reaction mixture containing a sample to be assayed by subtracting the amount of oxygen at the completion of reaction from the one at the beginning of reaction, and estimating the amount of Amadori compound in the sample by referring to the said calibration curve. Specifically, the determination procedures are similar to those described in "Titration of PAOD-L Activity" below, wherein a reaction mixture contains 1 unit/ml FAOD-L and a diluted solution of test sample, and the amount of oxygen consumed is measured.

The assay of the present invention can be carried out using a sample solution as it is though, it may be sometimes preferred to treat the sample so as to liberate lysine residue to which sugar is bound before the measurement. For such a purpose, the sample is treated with a protease (enzymic method) or a chemical substance such as hydrochloric acid, etc. (chemical method). The enzymic method is preferred and any of known proteases can be used in the present assay, for example, trypsin, carboxypeptidase B, papain, aminopeptidase, chymotrypsin, thermolysin, subtilisin, proteinase K, pronase and the like. The method of the enzyme treatment is also known and, for example, the protease treatment can be conducted as described in Examples below.

As described above, the culture obtained by growing the transformant capable of expressing FAOD-L of the present invention and processed materials thereof are highly specific to fructosyl lysine contained in glycated protein and are useful in the diagnosis and control of conditions of diabetes, which comprise measuring glycated proteins in blood sample. Further, they also show specific activity on fructosyl valine and are useful in the assay of glycated hemoglobin.

When blood (e.g. whole blood, plasma or serum) is to be assayed, a blood sample derived from a living body can be used as it is or after pre-treatment such as dialysis, etc.

FAOD-L of the present invention can be used in a solution or in a solid phase using an appropriate support. For example, an automated device equipped with a column packed with beads to which the enzyme is immobilized would contribute to the development of an efficient routine assay such as clinical examination, where a lot of specimens must be tested rapidly. Further, the immobilized enzyme is preferred in view of economical efficiency because it can be used repeatedly.

It is also possible to provide a kit by combining an enzyme(s) (e.g., FAOD-L, peroxidase, etc.) with a color-developing reagent(s) in an appropriate manner. Such a kit is useful for both of clinical assay and food analysis of Amadori compounds.

The immobilization of the enzyme can be conducted by a method known in the art, for example, carrier bonding method, cross-linkage method, inclusion method, complexing method, and the like. Examples of carriers include polymer gel, microcapsule, agarose, alginic acid, carrageenan, and the like. The enzyme can be bound to a carrier through covalent bond, ionic bond, physical absorption, biochemical affinity, etc. according to a method known in the art.

When using immobilized enzyme, the assay may be carried out in flow or batch system. As described above, the immobilized enzyme is particularly useful for a routine assay (clinical examination) of glycated proteins in blood samples. When the clinical examination is directed to the diagnosis of diabetes, the result as criterion for diagnosis of diabetes is expressed in concentration of glycated protein, or glycation rate which is the ratio of the concentration of glycated protein to that of whole protein in the sample. The whole protein concentration can be determined in a conventional manner, for example, through the measurement of absorbance at 280 nm, Lowry method, natural fluorescence of albumin, and the like.

The following Examples further illustrate the present invention in detail but are not to be construed to limit the scope thereof. Throughout the Examples below, plasmids, enzymes including restriction enzymes, T4 DNA ligase and the like were purchased from commercial sources and used in accordance with the supplier's instructions. The procedures which are not specifically described, e.g., cloning of DNA, construction of plasmids or vectors, transformation of host cells, cultivation of transformants, recovery of product from the cultured medium, and the like, were conducted substantially in accordance with a method known in the art or that taught in literatures. The enzymic activity can be evaluated in the following manner.

Titration of FAOD-L Activity (1) Method based on the colorimetric determination of generated hydrogen peroxide A. Measurement of generation rate A 100 mM FZL ($N^\alpha$-Z-lysine) solution was prepared by dissolving previously-obtained FZL in distilled water. To a mixture of 100 μl of 45 mM 4-aminoantipyrine, 100 μl of peroxidase (60 U/ml), 100 μl of 60 mM phenol, 1 ml of 0.1 M Tris-HCl buffer (pH 8.0) and 50 μl of enzyme solution was added distilled water to give a total volume of 3.0 ml. The solution was incubated for 2 min at 30° C. After adding 50 μl of 100 mM FZL solution, the time course of absorbance at 505 nm was measured. The amount (μmole) of hydrogen peroxide generated per minute was calculated on the basis of molar absorptivity ($5.16 \times 10^3$ $M^{-1}cm^{-1}$) of quinone pigment produced. The resultant numerical value was taken as a unit (U) of enzyme activity.

B. End point method

According to the same manner as that described in the method A above, a solution was prepared and a substrate solution was added thereto. After 30-minute-incubation at 30° C., absorbance at 505 nm was measured. The enzyme activity was evaluated on the basis of the amount of hydrogen peroxide generated referring to a calibration curve previously obtained using a standard hydrogen peroxide solution.

(2) Method based on the oxygen absorption due to enzyme reaction

To a mixture of 1 ml of 0.1 M Tris-HCl buffer (pH 8.0) and 50 μl of an enzyme solution was added distilled water to obtain a solution of a total volume of 3.0 ml. The resulting solution was charged in a cell of an oxygen electrode manufactured by Lank Brothers Co. The solution was stirred at 30° C. to allow the dissolved oxygen to be equilibrated under the temperature and 100 μl of 50 mM FZL was added to it. Then, the oxygen absorption was continuously measured on a recorder to obtain an initial rate. The amount of oxygen absorbed for one minute was determined on the basis of a calibration curve, which was taken as an enzyme unit.

In the following Examples, the titer of FAOD-L activity of cell culture or a processed material such as cell-free extract or purified enzyme was determined according to the method described in (1), "A. Measurement of generation rate", unless otherwise noted.

EXAMPLE 1

Cloning of DNA Encoding FAOD-L

1. Determination of Partial Amino Acid Sequence of FAOD-L from *A. terreus* GP1 (FERM BP-5684)

1) Fermentation of *A. terreus* GP1 (FERM BP-5684) and Purification of FAOD-L

*A. terreus* GP1 was inoculated into a 10 l of a medium (pH 6.0, 10 L) containing 0.5% FZL, 1.0% glucose, 0.1% $K_2HPO_4$, 0.1% $NaH_2PO_4$, 0.05% $MgSO_4$ $7H_2O$, 0.01% $CaCl_2$ $2H_2O$ and 0.2% yeast extract, and grown at 28° C. for 24 hr with aeration (2 L/min) with a jar fermentor. The culture was filtered to harvest mycelia.

A portion of mycelia (259 g, wet weight) was suspended in 800 ml of 0.1 M Tris-HCl buffer (pH 8.5) containing 2 mM DTT and ground with Dino-Mill. The ground mixture was centrifuged at 9,500 rpm, 4° C. for 20 min to obtain the supernatant (cell-free extract) as a crude extract, which was then subjected to purification.

To the crude extract was added ammonium sulfate to 40% saturation and the mixture was centrifuged at 12,000 rpm, 4° C. for 10 min. To the supernatant was added ammonium sulfate to 75% saturation, followed by centrifugation at 12,000 rpm, 4° C. for 10 min. The precipitates were dissolved in 50 mM Tris-HCl buffer (pH 8.5) containing 2 mM DTT (hereinafter, referred to as "buffer A"). After addition of an equal volume of buffer A containing 40% ammonium sulfate, about 200 ml of butyl-TOYOPEARL (TOYOBO) resin was added to the solution and stirred gently. The resin was washed with the same buffer, followed by elution with buffer A by batch method. The eluate was concentrated with ammonium sulfate, adsorbed onto a phenyl-TOYOPEARL column (TOYOBO) equilibrated with buffer A containing 25% saturation of ammonium sulfate. The column was washed with the same buffer, and eluted with a linear gradient of 25 to 0% saturation of ammonium sulfate. The active fractions were pooled and concentrated with ammonium sulfate, and adsorbed onto a butyl-TOYOPEARL column equilibrated with the buffer A containing 40% saturation of ammonium sulfate. The column was washed with the same buffer, and eluted with a linear gradient of 40 to 0% saturation of ammonium sulfate. Active fractions were combined and applied to DEAE-TOYOPEARL column (TOYOBO) equilibrated with the buffer A. FAOD activity was detected in washing fractions, which were pooled and concentrated with ammonium sulfate. The concentrate was purified by gel filtration with Sephacryl S-300 column equilibrated with 0.1 M Tris-HCl buffer (pH 8.5) containing 0.1 M NaCl and 2 mM DTT to give an enzyme preparation of 70 to 100 units.

Figure 6:
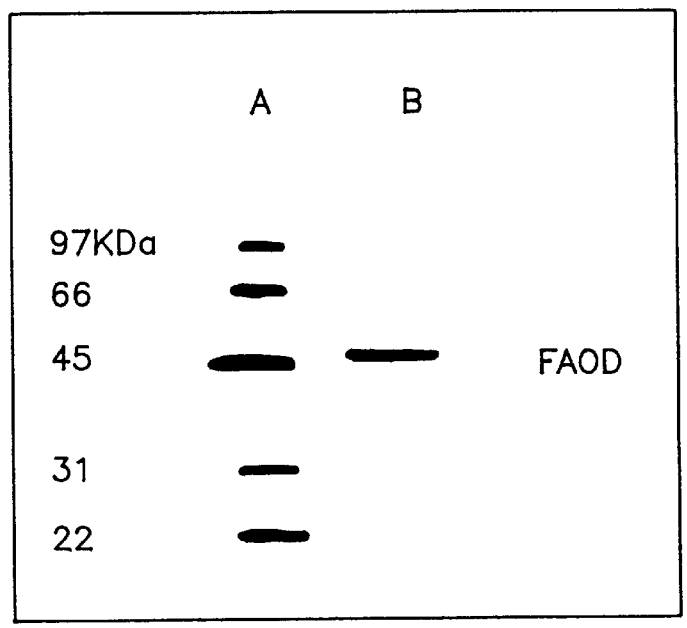
FIG. 6 shows the migration pattern obtained by subjecting FAOD-L purified from *A. terreus* GP1 (FERM BP-5684) to sodium dodecyl sulfate-polyacrylamide gel electrophoresis (SDS-PAGE).

The resultant enzyme was subjected to SDS-PAGE according to the Davis's method using 10% gel at 40 mA for 3 hours and staining protein with Coomassie brilliant blue G-250. Molecular weight was determined on the basis of calibration curve obtained by electrophoresing several standards such as phosphorylase B, bovine serum albumin, ovalbumin, carbonic anhydrase and soybean trypsin inhibitor in the same manner. As a result, the molecular weight of a subunit was about 48,000 daltons (48 kDa) (FIG. 6).

Figure 7:
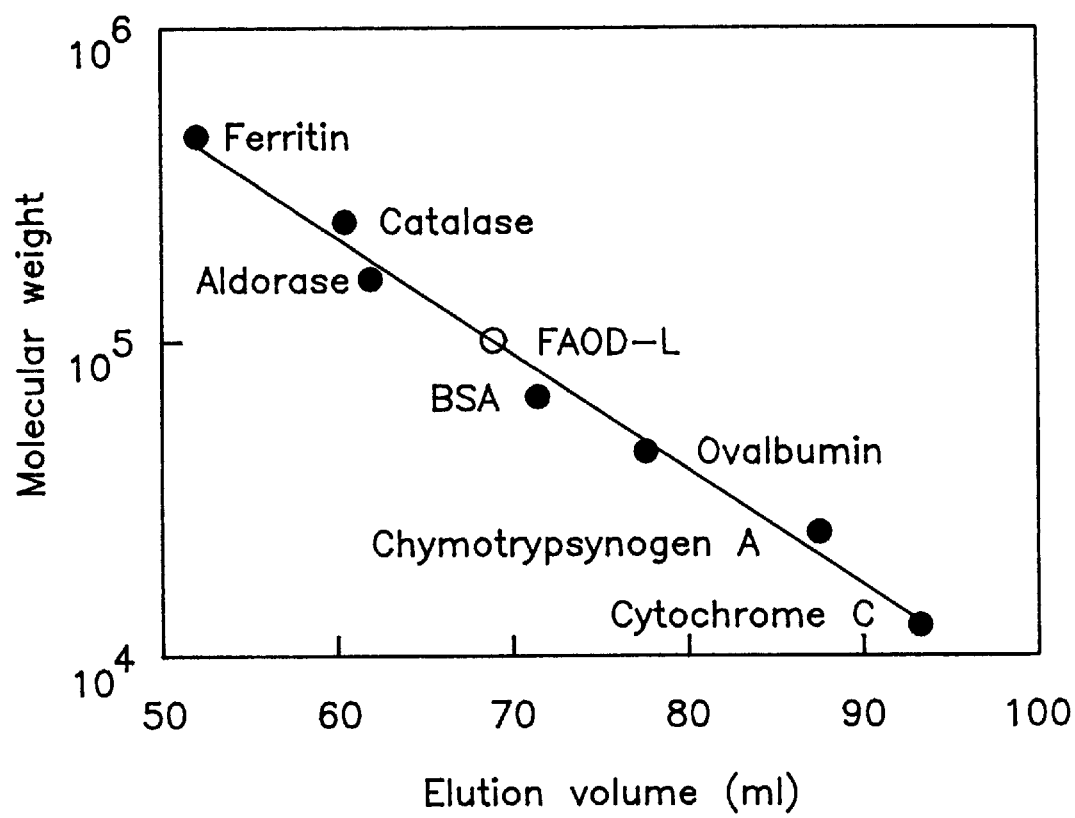
FIG. 7 is a graph showing the measurement of molecular weight of FAOD-L purified from *A. terreus* GP1 (FERM BP-5684) by gel filtration on Superdex 200 pg.

The gel filtration on Superdex 200 pg revealed that the molecular weight of FAOD-L to be about 94,000 daltons (94 kDa) as shown in FIG. 7.

2) Determination of Partial Amino Acid Sequence

The enzyme preparation purified in 1) above was digested with V8 protease (Sigma), and then fragmentated by Cleaveland method (G. W. Cleaveland, S. G. Fisher, M. W. Kirschner and U. K. Laemmli, *J. Biol. Chem.*, 252, 1102, 1977). Fragments were transferred onto PVDF (polyvinilidene fluoride, Milipore, trademark; Immobilon-PSQ) at 14 V overnight (12 hr), and sequenced by Edman degradation method with a protein sequencer 476A (Applied Biosystems). As a result, 17- and 15-amino acid sequences of N-terminal- and internal-peptide fragments were obtained. They are shown in SEQ ID Nos: 4 and 5, respectively.

2. Amplification of Partial cDNA Fragments by RT-PCR

1) Preparation of oligonucleotide primer

Primers for polymerase chain reaction (PCR) were designed on the basis of the nucleotide sequences deduced from the amino acid sequences obtained in 1. 2) above (FIG. 1), with taking the codon usage of Aspergillus into consideration. Further, BamHI recognition sequence was added at a terminus of a primer so as to facilitate the subcloning. The nucleic acid sequence of the primers 1 and 2 are shown in SEQ ID Nos: 6 and 7, respectively. The primer 2 is synthesized from the C-terminus on the basis of the nucleic acid sequence shown in FIG. 1 so that it can hybridize with a DNA complementary to a DNA with which the primer 1 hybridizes.

2) Synthesis of Total RNA

Total RNA (5 mg) was prepared from 1 g of mycelia obtained from *A. terreus* GP1 grown in a manner similar to that described in 1. 1) above according to the guanidine/phenol/chloroform method (Chomczynski, P. and Sacchi, N., Single-step method of RNA isolation by acid guanidinium thiocyanate-PhOH-chloroform extraction, *Anal. Biochem.*, 162, 156–159 (1987)).

3) RT-PCR

The reverse transcription polymerase chain reaction (RT-PCR) was carried out using the primers described in 2. 1) and the total RNA prepared in 2.2) above in the following manner.

a) To 2 μl of total RNA (5μg/μl) is added 36 μl of sterilized water, the mixture is heated at 65° C. for 5 min, and cooled on ice promptly.

b) To the solution of a) above are added 20 μl of 5×buffer, 5 μl of dNTPmix (20 mM for each), 2 μl of 115 U/ml RNase inhibitor, 24 μl of 0.42 μg/μl of oligo dT, 1 μl of 200 U/μl RTase (MLV), 10 μg of 0.1 M DTT.

c) The mixture of a) and b) is allowed to leave for 10 min at 25° C., reacted overnight at 42° C., heated at 95° C. for 5 min, and cooled on ice promptly to obtain cDNA.

d) The so obtained cDNA is mixed with a solution containing 2.5 μl of 10× PCR buffer, 1.8 μl of dNTP mix, 1 μl of primer 1, 1 μl of primer 2 and 16.575 μl of sterilized water.

e) The solution of d) is heated at 95° C. for 5 min, cooled on ice promptly, and 0.125 μl or 5U/ml Taq DNA polymerase is added thereto.

f) The mixture of e) is layered with mineral oil and subjected to the PCR by repeating 30 times the reaction cycle (94° C., 1 min; 60° C., 2 min; and 72° C., 2 min), and treating at 72° C. for 3 min.

g) The reaction mixture of PCR is then subjected to agarose gel electrophoresis.

Figure 3:
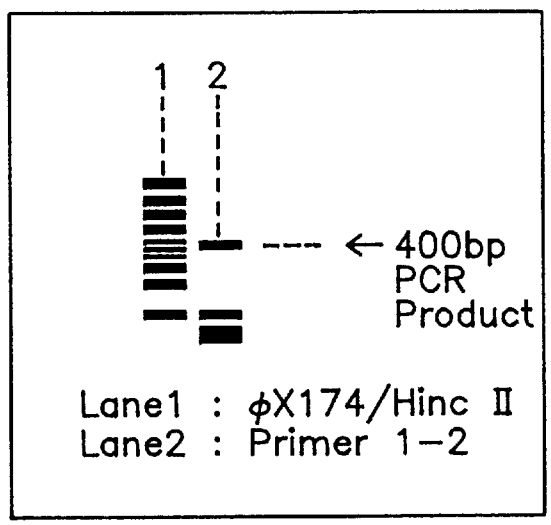
FIG. 3 shows the migration pattern on agarose gel electrophoresis of the products of RT-PCR, wherein lanes 1 and 2 correspond to the φx174/HincII (marker), and primers 1 and 2, respectively. The PCR was carried out using a total RNA obtained from *A. terreus* GP1 and the primers 1 and 2.

The result of electrophoresis is shown in FIG. 3. In FIG. 3, the lane 1 depicts the migration pattern of φx174/HincII used as a size marker for fragment amplified by PCR, aby PCR, and lane 2 depicts the result obtained using primers 1 and 2. As is clear from FIG. 3, about 400 bp fragment was amplified when primers 1 and 2 are used.

3. Subcloning of PCR Fragment

The purification of the about 400 bp PCR fragment was carried out by excising the gel containing the said fragment, charging it into a centrifuging tube having a filter for recovering DNA (0.22 μm diameter, Takara Shuzo, Code No. 9040), centrifuging at 10,000 rpm, 4° C. for 1 hr, and subjecting to ethanol precipitation.

The 1 μl of the PCR fragment was mixed with 1 μl of K buffer, 1 μl of BamHI and 7 μl of distilled water, and digested at 37° C. for 4 hr. The BamHI fragment was ligated to pBluescript II SK$^+$ (Stratagene), which is an expression vector for *E. coli* and contains lac promoter, at 16° C. for 30 min. The ligation mixture was used to transform *E. coli* JM109 with Takara Ligation Kit Ver. 2.0 (Takara Shuzo) by Hanahan method (Hanahan, D., Techniques for Transformation of *E. coli*, In: DNA Cloning, vol. I, Glover, D. M. (ed.), pp. 109–136, IRL Press, 1985).

Figure 4:
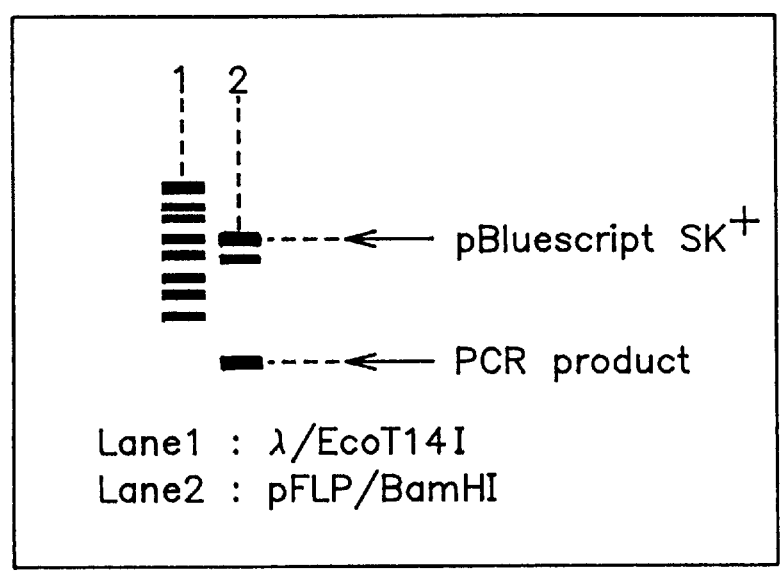
FIG. 4 shows the migration pattern on agarose gel electrophoresis of the products obtained by subcloning about 400 bp PCR fragment shown in FIG. 3, wherein lanes 1 and 2 show the migration patterns of λ/EcoT141 and pFLP/BamHI, respectively.

After growing transformants, one clone *E. coli* JM109/pFAL2 harboring plasmid pFAL2 comprising the about 400 bp PCR fragment inserted at the BamHI site of pBluescript II SK$^+$ (see, FIG. 4). In FIG. 4, lanes 1 and 2 show the migration patterns of λ/EcoT141 (marker) and pFLP/BamHI, respectively. The nucleic acid sequence, when determined by dideoxy method, proved to be identical with a partial sequence of FAOD-L cDNA.

4. Construction of cDNA Library and Plaque Hybridization

From the total RNA obtained in 2. 2) above was purified mRNA with mRNA Purification Kit (Pharmacia). The mRNA (5 μg) was then converted into cDNA using a reverse transcriptase. The cDNA was then ligated to λZAPII vector, followed by in vitro packaging with Gigapack III Gold (Stratagene) to obtain a cDNA library under the conditions indicated in the manual attached thereto. The titer of the cDNA was $1.0 \times 10^5$ pfu/μg vector.

Strains of E. coli XLI-Blue MRF were infected with the phage library obtained above and grown at 37° C. for 12 hr until plaques are formed. The library was screened by plaque-hybridization using $^{32}$P-labeled PCR fragment subcloned in 3. above. The plaques were transferred onto nitrocellulose filter, denatured with alkaline and hybridized with $^{32}$P-labeled probe at 42° C. for 12 hr. After washing, the filter was exposed to X-ray film for 12 hr. Twelve positive clones were identified from about 20,000 plaques.

5. Subcloning of DNA Encoding FAOD-L

The subcloning of a DNA encoding FAOD-L was carried out by in vitro excision method. Seven positive clones were transformed into E. coli JM109 Competent Cell (Takara Shuzo) using ExAssist helper phage (Stratagene) according to the manual attached thereto. Plasmids were extracted from the resultant transformants and subjected to determination of nucleic acid sequence to obtain a clone (E. coli JM109/pFAL2) containing plasmid pFAL2 to which about 1.5 kb DNA fragment having a nucleic acid sequence corresponding to the N-terminal amino acid sequence of FAOD-L. The schematic restriction map of plasmid pFAL2 is shown in FIG. 2. The nucleic acid sequence and deduced amino acid sequence of the clone pFAL2 are shown in SEQ ID Nos. 2 and 1, respectively.

The plasmid pFAL2 was transformed into E. coli SOLR (Stratagene) to obtain a transformant E. coli SOLR/pFAL2, which has been deposited at the "National Institute of Bioscience and Human-Technology, Agency of Industrial Science and Technology", Tsukuba-shi, Ibarakiken, Japan under the accession number of FERM BP-5981 since Jun. 16, 1997.

EXAMPLE 2

FAOD-L Activity of E. coli JM109/pFAL2

E. coli JM109/pFAL2 was grown in 50 ml LB medium (1% Bacto-Trypton, 0.5% Bacto-yeast extract, 1% NaCl, pH 7.2) containing 0.1 mM IPTG (isopropyl-β-D-galactopyranoside). IPTG was added to the medium 2 hours after inoculation of E. coli JM109/pFAL2.

After cultivation, cells were harvested by centrifugation (10,000 rpm, 4° C., 1 min). The cell pellet was washed with 0.85% KCl and suspended in 0.1 M Tris-HCl buffer (pH 8.0). Cells were ground 6 times with beads using MINI-BEAT BEATER (Japan LAMBDA) at 3,800 rpm, 30 seconds while intermittently ice-cooling, which was followed by centrifugation (1,400 rpm, 4° C., 5 min) to obtain cell-free extract. The titer of FAOD-L activity of the cell-free extract was carried out by the method described in item A above. As a control, a cell-free extract obtained by growing E. coli transformed with plasmid pBluescript II SK⁻ in a similar manner. FAOD-L activity of each cell-free extract and that of the culture of A. terreus GP1 are shown in Table 1 below.

TABLE 1

Expression of FAOD-L by
E. Coli JM109 Transformed with Plasmid pFAL2

| Strain | Specific activity (U/mg) | |
| --- | --- | --- |
| | +IPTG | −IPTG |
| JM109/pFAL2 | 0.178 | 0.0212 |
| JM109/pBluescript II SK⁻ | N.D. | — |
| A. terreus GP1 | | 0.135 |

N.D.: not detectable

As is clear from the Table 1, pFAL2 contains cDNA encoding FAOD-L and the E. coli transformed with the expression vector pFAL2 produces FAOD-L.

Figure 5:
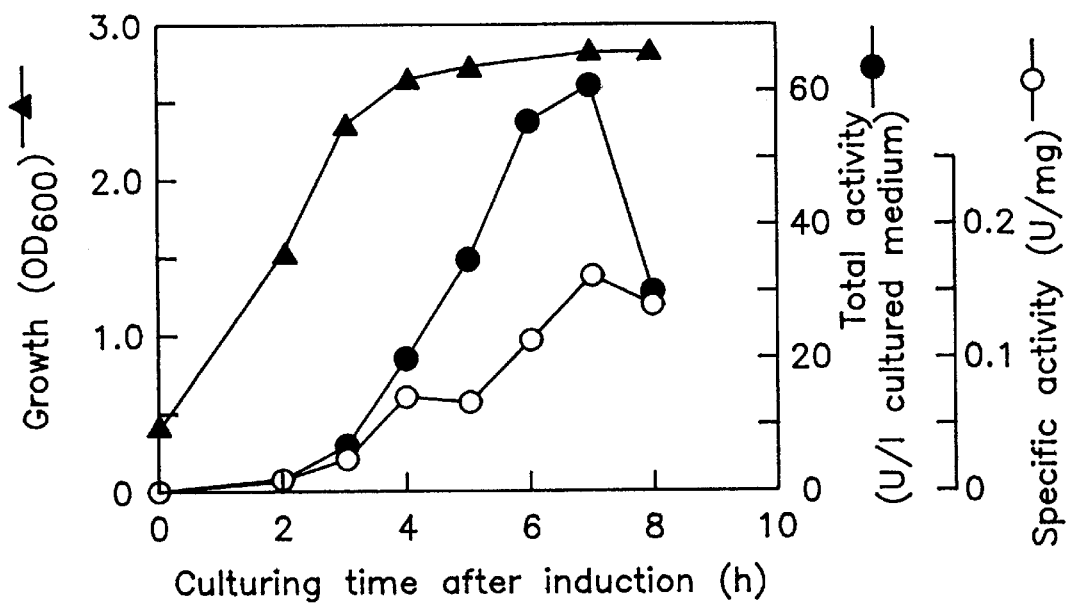
FIG. 5 is a graph showing the time-course of FAOD-L activity produced by *E. coli* host cells transformed with plasmid pFAL2, wherein the growth of the transformants ($OD_{600}$) is plotted on the vertical axis and time after induction with IPTG on the abscissa. The solid circle indicates the total activity (U/l), open circle the specific activity (U/mg), and solid triangle the cell growth ($OD_{600}$).

The time-course of FAOD-L production by E. coli transformed with plasmid pFAL2 is shown in FIG. 5, wherein the growth of the transformants ($OD_{600}$) is plotted on the vertical axis and time after induction with IPTG on the abscissa. The solid circle indicates the total activity (U/l), the open circle the specific activity (U/mg), and the solid triangle the cell growth ($OD_{600}$).

EXAMPLE 3

FAOD-L Activity of E. coli SOLR/pFAL2

E. coli SOLR/pFAL2 (FERM BP-5981) obtained in Example 1 was grown in 50 ml LB medium (1% Bacto-Trypton, 0.5% Bacto-yeast extract, 1% NaCl, pH 7.2) containing 0.1 mM IPTG. IPTG was added to the medium 2 hours after inoculation of E. coli SOLR/pFAL2.

After cultivation, cells were harvested by centrifugation (10,000 rpm, 4° C., 1 min). The cell pellet was washed with 0.85% KCl and suspended in 0.1 M Tris-HCl buffer (pH 8.0). Cells were ground 6 times with beads using MINI-BEAT BEATER (Japan LAMBDA) at 3,800 rpm, 30 seconds while intermittently ice-cooling, which was followed by centrifugation (1,400 rpm, 4° C., 5 min) to obtain cell-free extract. The titration of FAOD-L activity of the cell-free extract was carried out by the method described in "(1) A." above. As a control, a cell-free extract obtained by growing E. coli transformed with plasmid pBluescript II SK⁻ in a similar manner. FAOD-L activity of each cell-free extract and that of the culture of A. terreus GP1 are shown results are shown in Table 2 below.

TABLE 2

Expression of FAOD-L by
E. Coli SOLR Transformed with Plasmid pFAL2

| Strain | Specific activity (U/mg) | |
| --- | --- | --- |
| | +IPTG | −IPTG |
| SOLR/pFAL2 | 0.172 | 0.0429 |
| SOLR/pBluescript II SK⁻ | N.D. | — |
| A. terreus GP1 | | 0.135 |

N.D.: not detectable

As is clear from the Table 2, pFAL2 contains cDNA encoding FAOD-L and the E. coli transformed with the expression vector pFAL2 produces FAOD-L.

EXAMPLE 4

Expression of FAOD-L in Yeast

1. Construction of an Expression Vector for Yeast

The expression vector pFAL2 for E. coli containing a cloned cDNA originated from A. terreus GP1 (FERM BP-5684) was obtained from E. coli JM109/pFAL2. The PCR was conducted using the so obtained plasmid pFAL2 as a template, and two primers (SEQ ID Nos: 7 and 8) each corresponding to the N-terminal and C-terminal regions of FAOD-L, respectively, by repeating 30 times the reaction cycle (94° C. 1 min; 60° C., 1 min; and 72° C., 3 min), and treating at 72° C. for 5 min. After agarose gel electrophoresis, the intended FAOD-L cDNA fragment was purified in a conventional manner.

Plasmid pNOTel (Japanese Patent publication (KOKAI) 5-344895; EP-0558024) was digested with restriction enzyme Not I, dephosphorylated with bovine intestine phosphatase (Behringer Mannheim), and blunt-ended together with the FAOD-L cDNA fragment above by the use of a DNA Ligation Kit (Takara Shuzo, & Co.). These fragments are then ligated with the DNA Ligation Kit (Takara Shuzo, & Co.) to obtain plasmid pNFL.

The plasmid pNFL was then used for transforming *E. coli* JM109 in accordance with the Hanahan method (Hanahan, D., ibid.) Plasmids were prepared from 84 transformants randomly selected from the resultant transformants and restricted with the restriction enzyme HindIII to determine the orientation of the insert. As a result, plasmid pNFL8 wherein the FAOD-L cDNA fragment is inserted downstream from the AOD promoter was obtained.

FIG. 8 depicts the schematic restriction map of plasmid pNFL8.

2. Transformation

The plasmid pNFL8 was linearized by restriction enzyme BamHI and transformed into *C. boilinii* TK62, which is an auxotrophic strain for Ura, by modified lithium method. Because the plasmid pNOTel used for the preparation of plasmid pNFL8 contains URA3 gene, the transformants can be selected on the basis of Ura requirement.

Transformants were spread on YNB medium. Fourteen strains were randomly selected from the resultant URA$^+$ transformants, inoculated to a basal medium containing 1.5% methanol, and grown at 28° C. for 3 days with shaking. After harvesting the cells, the FAOD-L were measured in accordance with the method A above. The results are shown in Table 3 below. The determination of the FAOD-L activity was conducted in accordance with the method described in the titration method (1), A. above.

TABLE 3

FAOD-L Activity of *C. boidinii* TK62 transformed with pNFL8

| Strain TK62/pNEL | Specific Activity (U/mg protein) | Strain TK62/pNEL | Specific Activity (U/mg protein) |
| --- | --- | --- | --- |
| 1 | 0.13 | 8 | N.D. |
| 2 | 0.13 | 9 | 0.12 |
| 3 | N.D.*1 | 10 | 0.13 |
| 4 | 0.15 | 11 | 0.17 |
| 5 | 0.15 | 12 | 0.16 |
| 6 | 0.13 | 13 | N.D. |
| 7 | 0.12 | 14 | 0.44 |
| Control*2 | N.D. | | |

Note:
*1: Not detectable
*2: *C. boidinii* TK62 transformed with pNOTel

As is seen from Table 3, FAOD-L activity was detected in 11 strains, and *C. boilinii* TK62/pNEL14 showed the highest activity.

(3) Southern Analysis of Transformants

Figure 9:
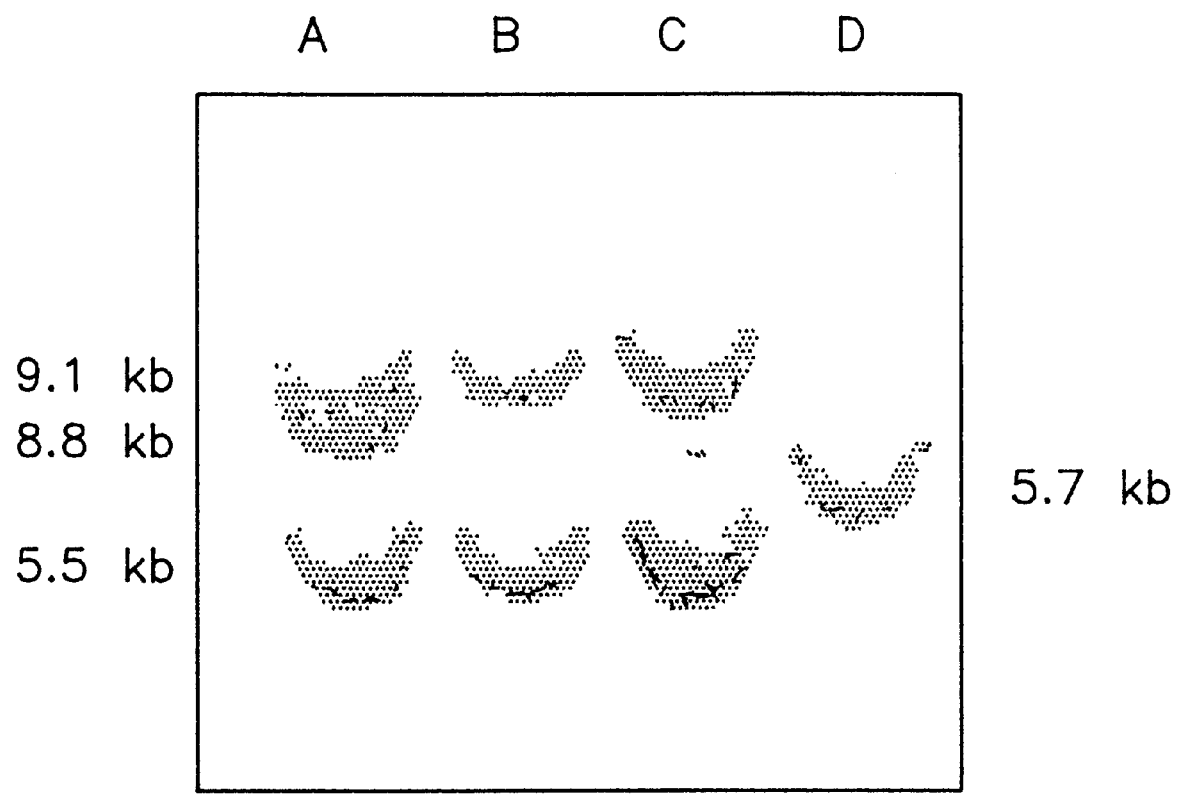
FIG. 9 shows the migration pattern on agarose gel electrophoresis showing the results of Southern analysis of chromosomal DNA of *C. boilinii* transformed with pNFL8.

The copy number of plasmids inserted into *C. boidinii* TK62 strains was analyzed by Southern blotting. Chromosomal DNA was extracted from each strain of three transformants with different activity. The DNA was digested with restriction enzyme EcoRI, electrophoresed on agarose gel, and southern blotted conventionally. As a probe, URA3 gene labeled by DIG-ELISA method was used. The result is shown in FIG. 9, wherein lanes A, B, C, D shows the migration pattern of DNA obtained from *C. boilinii* TK62/pNEL14, pNEL11, pNEL1 and *C. boilinii* S2 AOU-1, respectively. As can be seen from FIG. 9, the 8.8 kb fragment corresponding to the size of plasmid pNFL8 was detected only in the DNA from *C. boilinii* TK62/pNEL14 having the highest activity, which indicates that more than 2 copies of FAOD-L cDNA fragment have been inserted into chromosomal DNA of this strain. The said 8.8 kb fragment was not detected in the DNAs from other strains, indicating that only one single copy has been inserted into chromosomal DNA of other strains. Thus, if only one copy of plasmid pNFL8 has been inserted into a chromosomal DNA, the EcoRI treatment would not lead to the production of 8.8 kb fragment, but to the production of 9.1 kb fragment as is explained below. The 8.8 kb fragment could be generated due to the cleavage at two EcoRI recognition sites in pNFL8, which occurs when more than two copies are inserted in the plasmid. On the other hand, the 9.1 kb fragment could be generated due to the cleavage at EcoRI restriction sites of different origin, i.e., one from pNFL8 and the other from *C. boilinii*.

4. Conditions for Culturing Transformant Having FAOD-L Activity

The optimal conditions for culturing *C. boilinii* TK62/pNEL14 which proved to have the highest FAOD-L activity in 3. above was examined as follows. First, the transformant was grown in a basal medium containing different kinds of inorganic salt at 28° C. and the FAOD-L activity was measured. The results are shown in Table 4 below.

TABLE 4

Effect of Nitrogen Sources on the Production of FAOD-L by *C. boidinii* TK62/pNEL14

| N-Source | Activity (U/ml) | Specific Activity (U/mg) |
| --- | --- | --- |
| $NH_4NO_3$ | 1.57 | 0.549 |
| $NH_4Cl$ | 1.68 | 0.737 |
| $(NH_4)_2SO_4$ | 1.48 | 0.687 |
| $NaNO_3$ | 1.65 | 0.689 |

As can be seen from Table 4, it is preferred that the medium contains $NH_4Cl$ as nitrogen source at a concentration of 0.1 to 5.0%, preferably, 0.5 to 2.0%.

Second, *C. boilinii* TK62/pNEL14 was grown with changing the yeast concentration at 28° C. The results are shown in Table 5.

TABLE 5

Effect of Concentration of Yeast Extract on the Production of FAOD-L by *C. boidinii* TK62/pNEL14

| Yeast Extract (%) | Activity (U/ml) | Specific Activity (U/mg) |
| --- | --- | --- |
| 0.2 | 1.29 | 0.451 |
| 0.4 | 1.10 | 0.383 |
| 0.6 | 1.90 | 0.366 |
| 0.8 | 1.52 | 0.342 |
| 1.0 | 2.25 | 0.283 |

As can be seen from the Table 4, the FAOD-L activity increases when the medium contains yeast extract at higher concentration. It is preferred that the medium contains yeast extract at a concentration from 0.1 to 5.0%, more preferably, at about 1%.

Finally, the *C. boilinii* TK62/pNEL14 was grown in a medium containing, as a carbon source, 1.5% methanol, 1.5% methanol+3% glycerol, or 3% glycerol at 28° C. and the time-course of FAOD-L production was obtained. The results are shown in FIG. 10, wherein the growth of the transformants ($OD_{610}$) is plotted on the vertical axis and the culturing time on the abscissa, and the solid circle indicates the specific activity (U/mg) while the open circle the growth of cells ($OD_{610}$).

Figure 10:
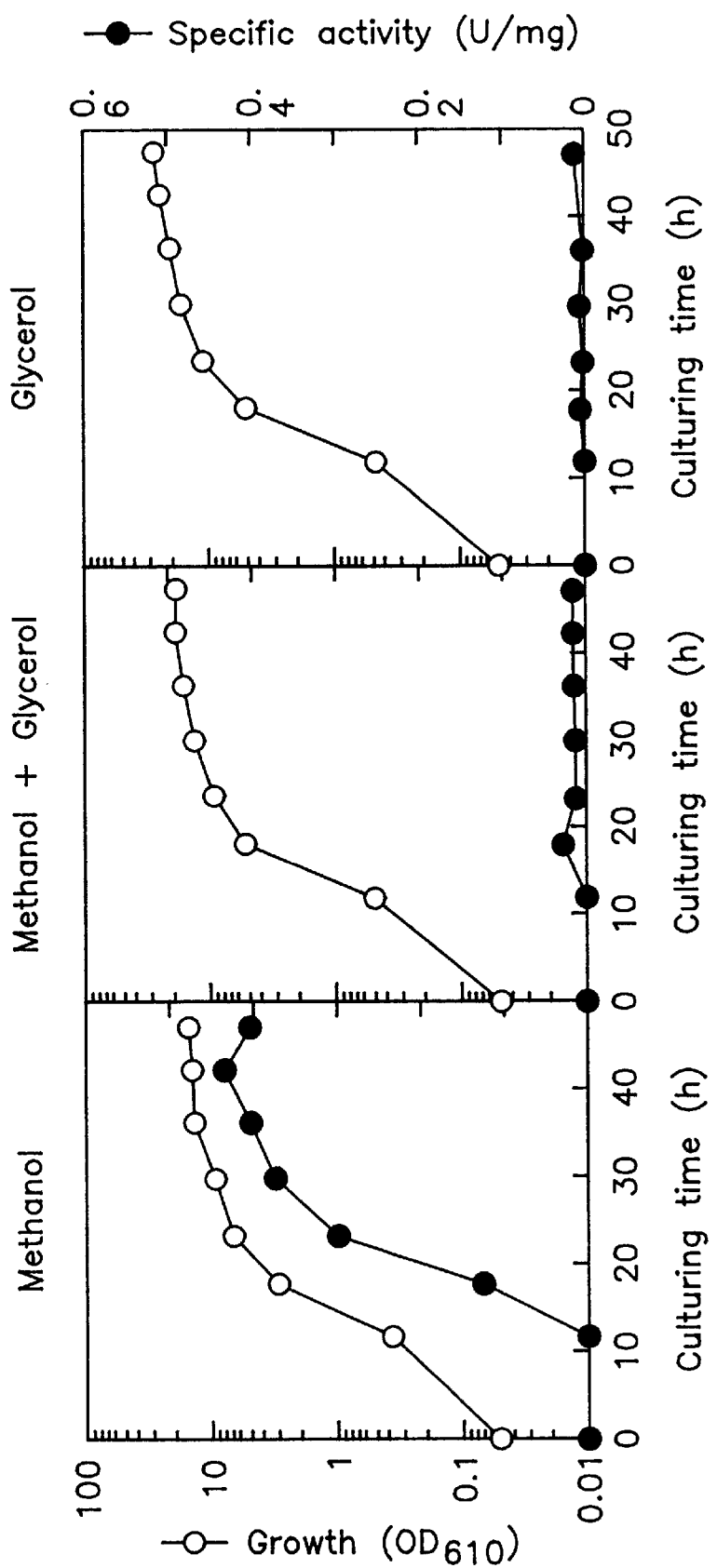
FIG. 10 is a graph showing the time-course of the production of FAOD-L activity by *C. boilinii* TK62/pNEL14 grown in a medium containing 1.5% methanol, 1.5% methanol+3% glycerol, or glycerol.

As is apparent from the FIG. 10, *C. boilinii* TK62/pNEL14, when cultured in a methanol medium (the right panel), produced FAOD-L to a remarkable extent. The maximum production was observed after 40-hour-cultivation.

The experimental results above demonstrates that a medium containing $NH_4Cl$ at a concentration of 0.1–5.0%, preferably 0.5–2.0% and/or yeast extract at a concentration of 0.1–5.0%, preferably 1% in a basal medium containing methanol at a concentration of 0.1 to 5.0%, preferably 1.5%.

5. Large-Scale Fermentation of C. boilinii TK62/pNEL14 with Jar-fermentor

Figure 11:
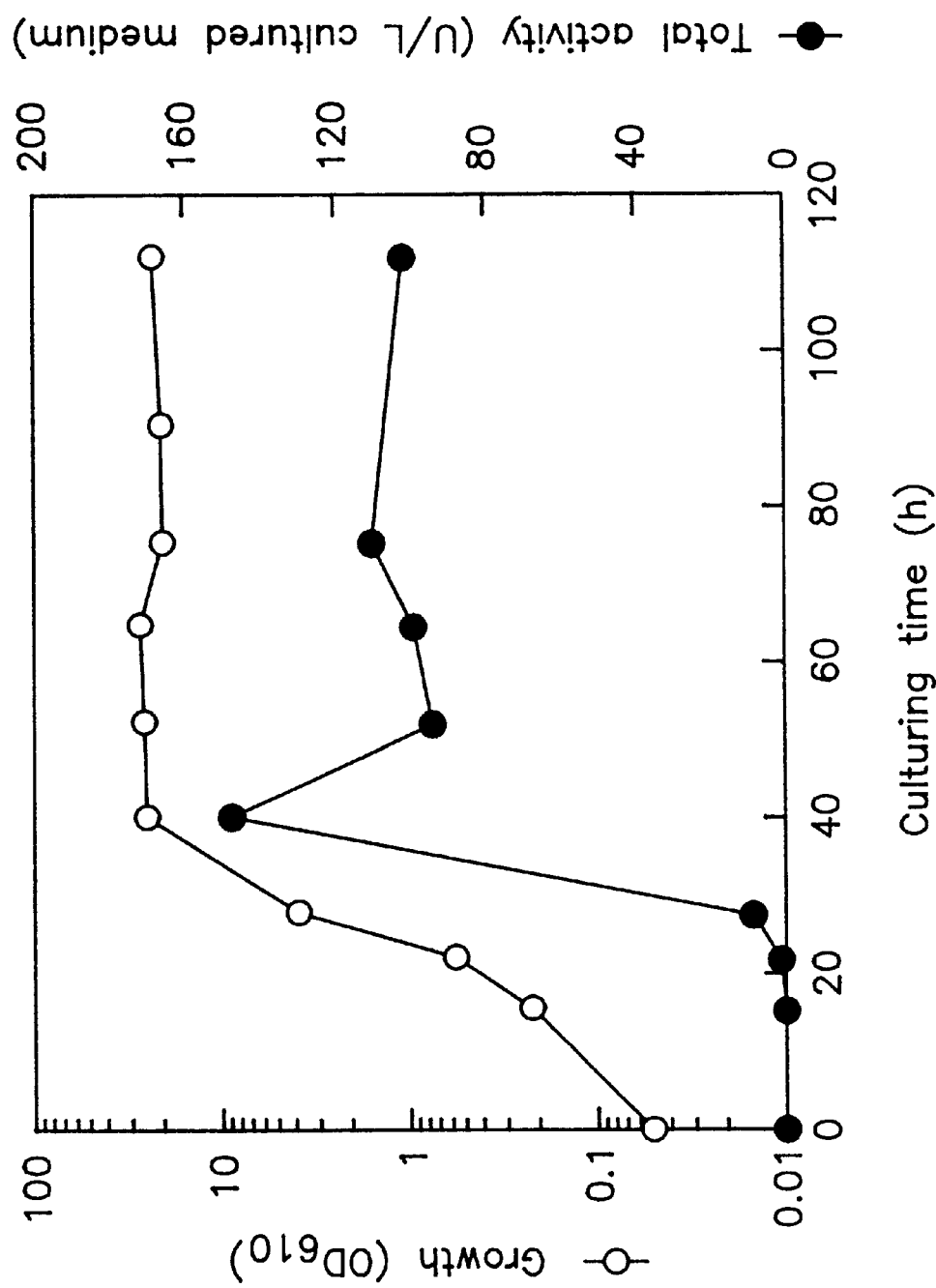
FIG. 11 is a graph showing the time-course of the production of FAOD-L activity by *C. boilinii* TK62/pNEL14 grown in a jar fermentor.

For large-scale production of FAOD-L, C. boilinii TK62/pNEL14 was grown in 1 L of medium in a 15 L jar fermentor. The medium was prepared by autoclaving a mixture (pH 6.0) containing 5 g of $NH_4Cl$, 5 g of $K_2HPO_4$, 1 g of $NaH_2PO_4$, 0.5 g of $MgSO_4$ $7H_2O$, 0.1 g of $CaCl_2$ $2H_2O$ and 10 g of yeast extract in 1 L at 120°0 C. for 20 min, and adding methanol to a concentration of 1.5%. The cells were cultured in the medium at 28° C. and the time-course of the production of FAOD-L activity by C. boilinii TK62/pNEL14 grown in a jar fermentor was depicted in FIG. 11, wherein the growth of the transformants ($OD_{610}$) is plotted on the vertical axis and the culturing time on the abscissa. The solid circle indicates the specific activity (U/mg) while the open circle the growth of cells ($OD_{610}$). As is apparent from the FIG. 11, the FAOD-L production reached maximum after 40-hour-cultivation and then decreased.

Cells were then harvested by centrifugation (10,000 rpm, 4° C., 1 min) and washed with 0.85% KCl and suspended in 0.1 M Tris-HCl buffer (pH 8.0). Cells were ground 6 times with beads using MINI-BEAT BEATER (Japan lambda) at 3,800 rpm, 30 seconds while intermittently ice-cooling, which was followed by centrifugation (1,400 rpm, 4° C., 5 min) to obtain cell-free extract. The cell-free extract was used as an enzyme solution in the following Examples.

EXAMPLE 5
Determination of the Amount of Glycated Human Albumin

A series of glycated human albumin solutions of different concentration between 0 and 10% were prepared by dissolving glycated human serum albumin (Sigma) in 0.9% sodium chloride solution. The measurement was carried out using the solutions in a following manner.
1) Protease-treatment A mixture of a glycated albumin solution (60 µl) and 12.5 mg/ml protease XIV (Sigma) solution (60 µl) was incubated at 37° C. for 30 min, followed by heating at about 90° C. for 5 min to stop the reaction.
2) Determination of Activity FAOD reaction mixture was prepared from the following reagents:

| | |
|---|---|
| 45 mM 4-Aminoantipyrine solution | 30 µl; |
| 60 mM N-Ethyl-N-(2-hydroxy-3-sulfopropyl)-m-toluidine solution | 30 µl; |
| Peroxidase solution (60 units/ml) | 30 µl; |
| 0.1 M Tris-HCl buffer (pH 8.0) | 300 µl; and |
| FAOD-L solution (6 units/ml) | 50 µl. |

Distilled water was added to make the total volume 1 ml.

Figure 12:
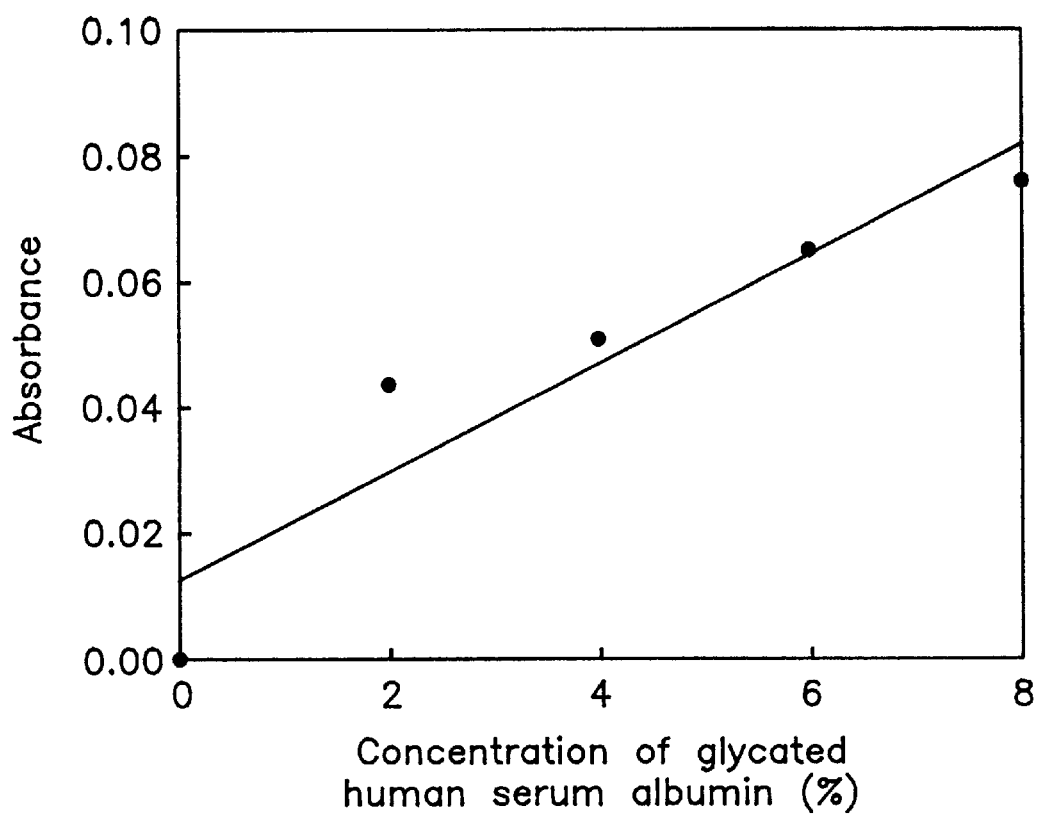
FIG. 12 is a graph showing the relation between the concentration of glycated human serum albumin as a substrate and the amount of hydrogen peroxide produced due to the FAOD action of a recombinant FLOD-L of the present invention.

FAOD-L solution (6 units/ml) was prepared by diluting the FAOD-L obtained in Example 4 with 0.1 M Tris-HCl buffer (pH 8.0). After incubating the FAOD reaction mixture at 30° C. for 2 min, 100 µl each of the protease-treated solution was added. Thirty minutes later, the absorbance at 555 nm was measured. The results are shown in FIG. 12, wherein the ordinate indicates the absorbance at 555 nm which corresponds to the amount of hydrogen peroxide generated and the abscissa the concentration of glycated albumin. FIG. 12 shows that the concentration of albumin and the amount of hydrogen peroxide are correlated.

EXAMPLE 6
Determination of Glycation Rate of Human Serum Albumin

Glycated human serum albumin (Sigma Co.) (150 mg) and human serum albumin (Sigma Co.) (150 mg) were separately dissolved in 0.9% sodium chloride solution (3 ml). These solutions were combined to prepare solutions of different glycation rate ranging from 24.6% to 61.1% when evaluated on automatic glycoalbumin measuring device (Kyoto Daiichi Kagaku Co. Ltd.). The measurement was carried out using these solutions in a following manner.
1) Protease-treatment A mixture of a glycated albumin solution (60 µl) and 12.5 mg/ml protease XIV (Sigma) solution (60 µl) was incubated at 37° C. for 30 min, followed by heating at about 90° C. for 5 min to stop the reaction.
2) Determination of Activity FAOD reaction mixture was prepared from the following reagents:

| | |
|---|---|
| 45 mM 4-Aminoantipyrine solution | 30 µl; |
| 60 mM N-Ethyl-N-(2-hydroxy-3-sulfopropyl)-m-toluidine solution | 30 µl; |
| Peroxidase solution (60 units/ml) | 30 µl; |
| 0.1 M Tris-HCl buffer (pH 8.0) | 300 µl; and |
| FAOD-L solution (6 units/ml) | 50 µl. |

Distilled water was added to make the total volume 1 ml.

FAOD-L solution (6 units/ml) was prepared by diluting the FAOD-L obtained in Example 4 with 0.1 M Tris-HCl buffer (pH 8.0) to a concentration of 6 units/ml.

Figure 13:
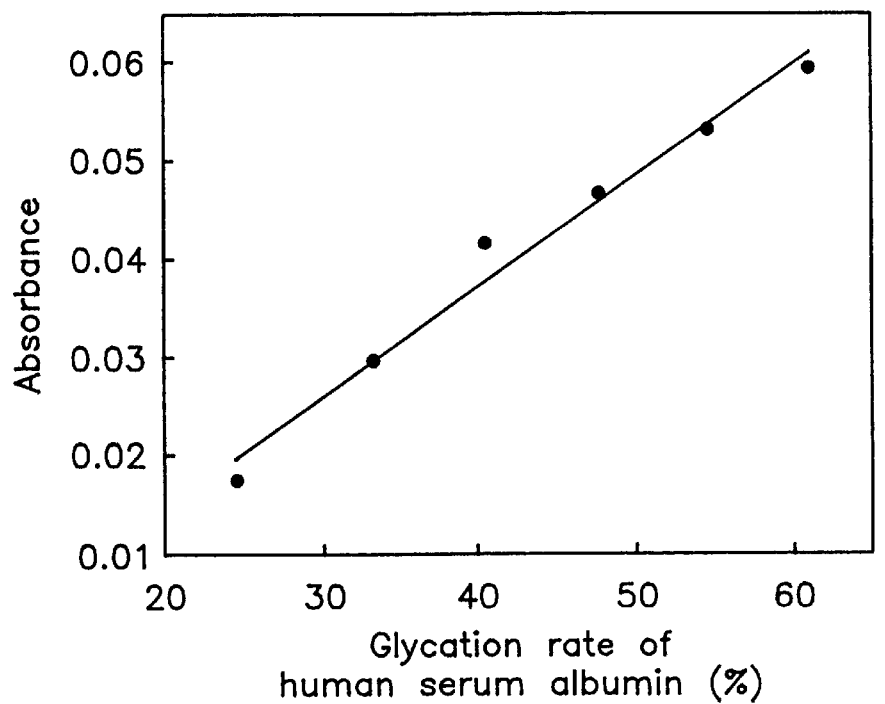
FIG. 13 is a graph illustrating the relation between the glycation rate of human serum albumin and the amount of hydrogen peroxide produced due to the FAOD action of a recombinant FLOD-L of the present invention.

After incubating FAOD reaction mixture at 30° C. for 2 min, 100 µl each of the protease-treated solutions was added. Thirty minutes later, the absorbance at 555 nm was measured. The results are shown in FIG. 13, wherein the ordinate indicates the absorbance at 555 nm which corresponds to the amount of hydrogen peroxide generated and the abscissa indicates the glycation rate of albumin. FIG. 13 shows that the glycation rate of albumin and the amount of hydrogen peroxide are correlated.

EXAMPLE 7
Determination of Glycated Hemoglobin Level

A series of glycated hemoglobin solutions of different concentration between 0 and 30% were prepared by dissolving glycohemoglobin control (Sigma) in distilled water. The measurement was carried out using these solutions in a following manner.
1) Protease-treatment A mixture of a glycated hemoglobin solution (25 µl), 500 units/ml aminopeptidase solution (5 µl) and 0.1 M Tris-HCl buffer (pH 8.0) (20 µl) was incubated at 30° C. for 30 min. To the mixture was added 10% trichloroacetic acid (50 µl) and stirred. After allowing to stand for 30 min at 0° C., the mixture was centrifuged at 12000 rpm for 10 min. The supernatant was neutralized with about 50 µl of 2M NaOH.
2) Determination of Activity FAOD reaction mixture was prepared from the following reagents:

| | |
|---|---|
| 3 mM N-Carboxymethylamino-2-phenylamine solution | 30 µl; |
| Peroxidase solution (60 units/ml) | 30 µl; |
| 0.1 M Tris-HCl buffer (pH 8.0) | 300 µl; and |
| FAOD-L solution (4 units/ml) | 10 µl. |

After combining the reagents, the total volume was adjusted to 1 ml with distilled water. FAOD solution (4 units/ml) was prepared by diluting the FAOD-L obtained in Example 4 with 0.1 M Tris-HCl buffer (pH 8.0).

Figure 14:
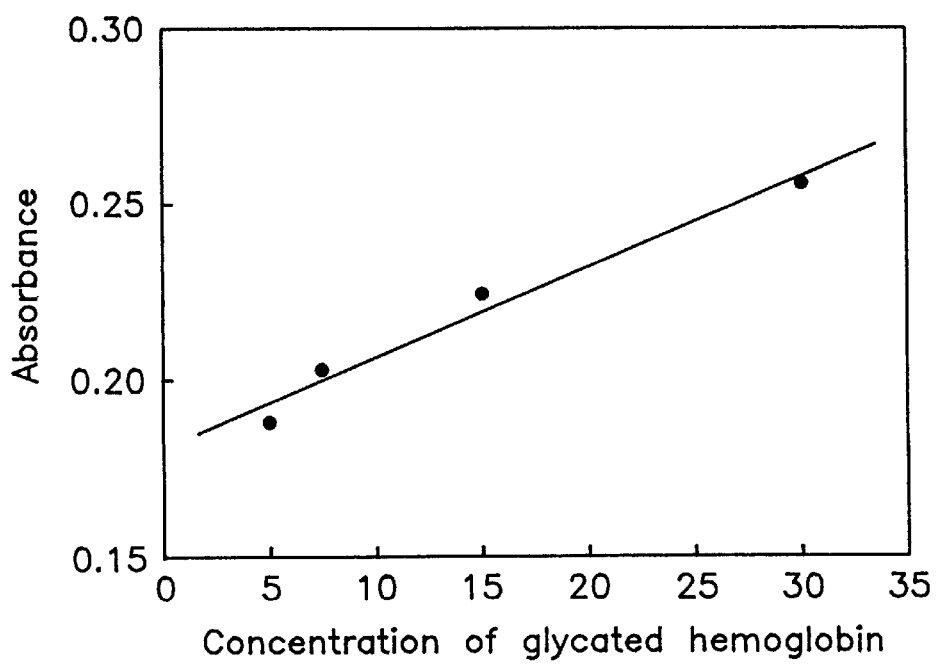
FIG. 14 is a graph illustrating a relation between concentration of the glycated hemoglobin and the amount of hydrogen peroxide produced due to the FAOD action of a recombinant FAOD-L of the present invention.

After incubating the FAOD reaction mixture at 30° C. for 2 min, each of protease-treated solution (80 μl) was added thereto. Thirty minutes later, the absorbance at 727 nm was measured. The results are shown in FIG. 14, wherein the ordinate indicates the absorbance at 727 nm which corresponds to the amount of hydrogen peroxide generated and the abscissa indicates the concentration of glycated hemoglobin. FIG. 14 shows that the concentration of the glycated hemoglobin and the amount of hydrogen peroxide are correlated.

---

What is claimed is:

1. An isolated DNA having the nucleotide sequence of SEQ ID No. 2 and encoding a protein having fructosyl amino acid oxidase activity.

2. An expression vector containing the DNA of claim 1.

3. A transformant obtained by transforming a host cell with the expression vector of claim 2.

4. The transformant of claim 3, which is a procaryotic or eucaryotic cell.

5. A process for producing a protein having fructosyl amino acid oxidase, which comprises culturing the transformant of claim 3 in a medium and recovering a protein having the fructosyl amino acid oxidase activity from the cultured medium.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 437 amino acids
      (B) TYPE: amino acid
      (C) STRANDEDNESS: Not Relevant
      (D) TOPOLOGY: linear (ii) MOLECULE TYPE: protein (xi) SEQUENCE DESCRIPTION: SEQ ID NO:1:

```
Met Pro Val Thr Lys Ser Ser Ser Ile Leu Ile Ile Gly Ala Gly Thr
1               5                   10                  15

Trp Gly Cys Ser Thr Ala Leu His Leu Ala Arg Arg Gly Tyr Thr Asn
                20                  25                  30

Val Thr Val Leu Asp Pro Tyr Pro Val Pro Ser Ala Ile Ser Ala Gly
            35                  40                  45

Asn Asp Val Asn Lys Ile Ile Ser Ser Gly Gln Tyr Ser Ser Lys Lys
        50                  55                  60

Asp Glu Val Glu Val Asn Glu Ile Ile Ala Glu Gln Ala Phe Asn Gly
65                  70                  75                  80

Trp Lys Asn Asp Pro Ile Phe Lys Pro Tyr Tyr His Asp Thr Gly Val
                85                  90                  95

Val Met Ser Ala Thr Thr Gln Glu Gly Leu Glu Arg Leu Gly Val Arg
            100                 105                 110

Val Arg Pro Glu Asp Glu Pro Asp Val Ala Glu Leu Thr Arg Pro Glu
        115                 120                 125

Gln Phe Arg Gln Leu Ala Pro Gly Val Leu Lys Gly Asn Phe Pro Gly
    130                 135                 140

Trp Arg Gly Tyr His Ile Arg Ser Asn Ala Gly Trp Ala His Ala Arg
145                 150                 155                 160

Asn Ala Leu Val Ala Ala Ala Arg Glu Ala Gln Arg Leu Gly Val Arg
                165                 170                 175

Phe Val Ala Gly Ser Pro Gln Gly Arg Val Ile Thr Leu Ile Phe Glu
            180                 185                 190

Asn Asn Asp Val Lys Gly Ala Val Thr Ala Asp Gly Lys Ile Trp Arg
        195                 200                 205

Ala Glu Gln Thr Ile Leu Cys Ala Gly Ala Ala Ala Gly Gln Phe Leu
    210                 215                 220

Asp Phe Lys Asp Gln Leu Arg Pro Thr Ala Trp Thr Leu Val His Ile
225                 230                 235                 240

Gln Leu Lys Pro Glu Glu Arg Ala Gln Tyr Lys Asn Met Pro Val Val
                245                 250                 255

Phe Asn Ile Glu Lys Gly Phe Phe Phe Glu Pro Asp Glu Glu Arg Gly
            260                 265                 270

Glu Ile Lys Ile Cys Asp Glu His Pro Gly Tyr Thr Asn Met Thr Thr
```

275                 280                 285
    Gly Ala Asp Gly Arg Val Arg Ser Ile Pro Phe Glu Lys Thr Gln Val
        290                 295                 300

Pro Arg Glu Ala Glu Met Arg Val Arg Lys Leu Leu Ser Glu Thr Met
    305                 310                 315                 320

Pro Gln Leu Ala Asp Arg Pro Phe Ser Phe Ala Arg Ile Cys Trp Cys
                    325                 330                 335

Ala Asp Thr Pro Asn Arg Glu Phe Ile Ile Asp Arg His Pro Glu Tyr
                340                 345                 350

Pro Ser Leu Val Leu Gly Cys Gly Ala Ser Gly Arg Gly Phe Lys Tyr
            355                 360                 365

Leu Pro Ser Ile Gly Ser Ile Ile Ala Asp Ala Met Glu Asp Lys Thr
    370                 375                 380

Pro Ala Lys Ile His Lys Leu Ile Arg Trp Ser Pro Glu Ile Ala Ile
    385                 390                 395                 400

Asn Arg Asn Trp Gly Asp Arg Leu Gly Arg Phe Gly Gly Pro Asn Arg
                    405                 410                 415

Val Met Asp Phe Asn Glu Val Lys Glu Trp Thr Asn Val Thr Gln Arg
                420                 425                 430

Asp Ile Ser Lys Leu
            435

(2) INFORMATION FOR SEQ ID NO:2:

(i) SEQUENCE CHARACTERISTICS:
        (A) LENGTH: 1314 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..1311

(xi) SEQUENCE DESCRIPTION: SEQ ID NO:2:

ATG CCA GTC ACC AAG TCT TCG TCG ATA TTG ATC ATC GGG GCG GGC ACC        48
    Met Pro Val Thr Lys Ser Ser Ser Ile Leu Ile Ile Gly Ala Gly Thr
    1               5                   10                  15

TGG GGT TGC TCA ACT GCC CTG CAT CTT GCC CGC AGA GGA TAC ACC AAT        96
    Trp Gly Cys Ser Thr Ala Leu His Leu Ala Arg Arg Gly Tyr Thr Asn
                    20                  25                  30

GTC ACT GTC CTT GAC CCG TAC CCG GTT CCA TCA GCC ATT TCG GCC GGC       144
    Val Thr Val Leu Asp Pro Tyr Pro Val Pro Ser Ala Ile Ser Ala Gly
                35                  40                  45

AAC GAC GTC AAC AAG ATC ATC TCG TCC GGC CAG TAC AGC AGC AAG AAG       192
    Asn Asp Val Asn Lys Ile Ile Ser Ser Gly Gln Tyr Ser Ser Lys Lys
    50                  55                  60

GAC GAG GTC GAA GTC AAT GAG ATT ATC GCC GAA CAG GCC TTC AAT GGC       240
    Asp Glu Val Glu Val Asn Glu Ile Ile Ala Glu Gln Ala Phe Asn Gly
    65                  70                  75                  80

TGG AAA AAT GAC CCC ATC TTC AAG CCG TAC TAC CAC GAC ACC GGC GTC       288
    Trp Lys Asn Asp Pro Ile Phe Lys Pro Tyr Tyr His Asp Thr Gly Val
                    85                  90                  95

GTG ATG TCC GCC ACC ACA CAG GAA GGA TTG GAG CGT CTG GGG GTC CGC       336
    Val Met Ser Ala Thr Thr Gln Glu Gly Leu Glu Arg Leu Gly Val Arg
                    100                 105                 110

GTG CGA CCT GAA GAT GAA CCC GAT GTA GCC GAA TTG ACT CGG CCG GAG       384
    Val Arg Pro Glu Asp Glu Pro Asp Val Ala Glu Leu Thr Arg Pro Glu
            115                 120                 125

```
CAG TTC CGC CAG CTG GCC CCC GGC GTC TTG AAG GGT AAC TTC CCC GGT      432
Gln Phe Arg Gln Leu Ala Pro Gly Val Leu Lys Gly Asn Phe Pro Gly
    130                 135                 140

TGG AGG GGG TAC CAC ATT CGC TCA AAC GCG GGC TGG GCG CAT GCG CGC      480
Trp Arg Gly Tyr His Ile Arg Ser Asn Ala Gly Trp Ala His Ala Arg
145                 150                 155                 160

AAC GCC CTG GTC GCC GCG GCG CGG GAG GCA CAG CGC CTG GGT GTG CGC      528
Asn Ala Leu Val Ala Ala Ala Arg Glu Ala Gln Arg Leu Gly Val Arg
                165                 170                 175

TTC GTC GCG GGA TCG CCG CAG GGC AGA GTC ATC ACG TTG ATT TTT GAG      576
Phe Val Ala Gly Ser Pro Gln Gly Arg Val Ile Thr Leu Ile Phe Glu
        180                 185                 190

AAC AAC GAT GTG AAG GGT GCC GTC ACG GCG GAC GGC AAG ATC TGG CGG      624
Asn Asn Asp Val Lys Gly Ala Val Thr Ala Asp Gly Lys Ile Trp Arg
            195                 200                 205

GCC GAG CAG ACT ATC CTC TGC GCT GGT GCG GCC GCC GGC CAG TTT CTG      672
Ala Glu Gln Thr Ile Leu Cys Ala Gly Ala Ala Ala Gly Gln Phe Leu
    210                 215                 220

GAT TTC AAG GAC CAA CTG CGT CCC ACT GCG TGG ACT CTG GTC CAC ATC      720
Asp Phe Lys Asp Gln Leu Arg Pro Thr Ala Trp Thr Leu Val His Ile
225                 230                 235                 240

CAG TTG AAG CCG GAA GAG CGT GCC CAG TAT AAA AAC ATG CCG GTG GTC      768
Gln Leu Lys Pro Glu Glu Arg Ala Gln Tyr Lys Asn Met Pro Val Val
                245                 250                 255

TTC AAC ATC GAG AAG GGG TTC TTC TTC GAG CCG GAT GAG GAG CGT GGT      816
Phe Asn Ile Glu Lys Gly Phe Phe Phe Glu Pro Asp Glu Glu Arg Gly
        260                 265                 270

GAA ATC AAG ATC TGC GAC GAA CAC CCC GGG TAC ACG AAT ATG ACC ACG      864
Glu Ile Lys Ile Cys Asp Glu His Pro Gly Tyr Thr Asn Met Thr Thr
            275                 280                 285

GGG GCC GAC GGC CGC GTG AGG AGC ATT CCC TTC GAG AAG ACG CAG GTT      912
Gly Ala Asp Gly Arg Val Arg Ser Ile Pro Phe Glu Lys Thr Gln Val
    290                 295                 300

CCT CGA GAA GCG GAG ATG CGC GTC CGC AAG CTT CTG TCT GAA ACG ATG      960
Pro Arg Glu Ala Glu Met Arg Val Arg Lys Leu Leu Ser Glu Thr Met
305                 310                 315                 320

CCT CAG CTT GCG GAC CGG CCG TTC AGT TTC GCA AGG ATC TGC TGG TGT     1008
Pro Gln Leu Ala Asp Arg Pro Phe Ser Phe Ala Arg Ile Cys Trp Cys
                325                 330                 335

GCG GAT ACC CCC AAT CGC GAG TTT ATC ATT GAC CGT CAT CCC GAA TAC     1056
Ala Asp Thr Pro Asn Arg Glu Phe Ile Ile Asp Arg His Pro Glu Tyr
        340                 345                 350

CCG TCG CTT GTT CTT GGG TGT GGT GCT TCA GGA CGA GGC TTC AAA TAT     1104
Pro Ser Leu Val Leu Gly Cys Gly Ala Ser Gly Arg Gly Phe Lys Tyr
            355                 360                 365

CTT CCC TCG ATC GGA AGC ATC ATC GCA GAC GCC ATG GAG GAC AAA ACC     1152
Leu Pro Ser Ile Gly Ser Ile Ile Ala Asp Ala Met Glu Asp Lys Thr
    370                 375                 380

CCG GCA AAA ATC CAC AAG CTG ATC CGC TGG AGC CCG GAA ATC GCG ATC     1200
Pro Ala Lys Ile His Lys Leu Ile Arg Trp Ser Pro Glu Ile Ala Ile
385                 390                 395                 400

AAC CGT AAC TGG GGG GAC AGA TTA GGT CGA TTT GGA GGG CCC AAC CGG     1248
Asn Arg Asn Trp Gly Asp Arg Leu Gly Arg Phe Gly Gly Pro Asn Arg
                405                 410                 415

GTC ATG GAT TTC AAT GAA GTG AAG GAG TGG ACT AAT GTC ACC CAA AGG     1296
Val Met Asp Phe Asn Glu Val Lys Glu Trp Thr Asn Val Thr Gln Arg
        420                 425                 430

GAC ATC TCG AAG TTA TAG                                              1314
Asp Ile Ser Lys Leu
            435
```

(2) INFORMATION FOR SEQ ID NO:3:

(i) SEQUENCE CHARACTERISTICS:
        (A) LENGTH: 437 amino acids
        (B) TYPE: amino acid
        (D) TOPOLOGY: linear (ii) MOLECULE TYPE: protein (xi) SEQUENCE DESCRIPTION: SEQ ID NO:3:

```
Met Pro Val Thr Lys Ser Ser Ile Leu Ile Ile Gly Ala Gly Thr
 1               5                  10                  15

Trp Gly Cys Ser Thr Ala Leu His Leu Ala Arg Arg Gly Tyr Thr Asn
                20                  25                  30

Val Thr Val Leu Asp Pro Tyr Pro Val Pro Ser Ala Ile Ser Ala Gly
                35                  40                  45

Asn Asp Val Asn Lys Ile Ile Ser Ser Gly Gln Tyr Ser Ser Lys Lys
 50                  55                  60

Asp Glu Val Glu Val Asn Glu Ile Ile Ala Glu Gln Ala Phe Asn Gly
 65                  70                  75                  80

Trp Lys Asn Asp Pro Ile Phe Lys Pro Tyr Tyr His Asp Thr Gly Val
                85                  90                  95

Val Met Ser Ala Thr Thr Gln Glu Gly Leu Glu Arg Leu Gly Val Arg
                100                 105                 110

Val Arg Pro Glu Asp Glu Pro Asp Val Ala Glu Leu Thr Arg Pro Glu
                115                 120                 125

Gln Phe Arg Gln Leu Ala Pro Gly Val Leu Lys Gly Asn Phe Pro Gly
                130                 135                 140

Trp Arg Gly Tyr His Ile Arg Ser Asn Ala Gly Trp Ala His Ala Arg
145                 150                 155                 160

Asn Ala Leu Val Ala Ala Arg Glu Ala Gln Arg Leu Gly Val Arg
                165                 170                 175

Phe Val Ala Gly Ser Pro Gln Gly Arg Val Ile Thr Leu Ile Phe Glu
                180                 185                 190

Asn Asn Asp Val Lys Gly Ala Val Thr Ala Asp Gly Lys Ile Trp Arg
                195                 200                 205

Ala Glu Gln Thr Ile Leu Cys Ala Gly Ala Ala Gly Gln Phe Leu
                210                 215                 220

Asp Phe Lys Asp Gln Leu Arg Pro Thr Ala Trp Thr Leu Val His Ile
225                 230                 235                 240

Gln Leu Lys Pro Glu Glu Arg Ala Gln Tyr Lys Asn Met Pro Val Val
                245                 250                 255

Phe Asn Ile Glu Lys Gly Phe Phe Glu Pro Asp Glu Glu Arg Gly
                260                 265                 270

Glu Ile Lys Ile Cys Asp Glu His Pro Gly Tyr Thr Asn Met Thr Thr
                275                 280                 285

Gly Ala Asp Gly Arg Val Arg Ser Ile Pro Phe Glu Lys Thr Gln Val
                290                 295                 300

Pro Arg Glu Ala Glu Met Arg Val Arg Lys Leu Leu Ser Glu Thr Met
305                 310                 315                 320

Pro Gln Leu Ala Asp Arg Pro Phe Ser Phe Ala Arg Ile Cys Trp Cys
                325                 330                 335

Ala Asp Thr Pro Asn Arg Glu Phe Ile Ile Asp Arg His Pro Glu Tyr
                340                 345                 350

Pro Ser Leu Val Leu Gly Cys Gly Ala Ser Gly Arg Gly Phe Lys Tyr
```

```
                     355                 360                 365
Leu Pro Ser Ile Gly Ser Ile Ile Ala Asp Ala Met Glu Asp Lys Thr
    370                 375                 380

Pro Ala Lys Ile His Lys Leu Ile Arg Trp Ser Pro Glu Ile Ala Ile
385                 390                 395                 400

Asn Arg Asn Trp Gly Asp Arg Leu Gly Arg Phe Gly Gly Pro Asn Arg
                405                 410                 415

Val Met Asp Phe Asn Glu Val Lys Glu Trp Thr Asn Val Thr Gln Arg
                420                 425                 430

Asp Ile Ser Lys Leu
                435
```

(2) INFORMATION FOR SEQ ID NO:4:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:4:

```
Pro Val Thr Lys Ser Ser Ser Ile Leu Ile Ile Gly Ala Gly Thr Trp
1               5                   10                  15

Gly
```

(2) INFORMATION FOR SEQ ID NO:5:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Leu Thr Arg Pro Glu Gln Phe Arg Gln Leu Ala Pro Gly Val Leu Lys
1               5                   10                  15
```

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:6:

```
YTNATHATHG GNGCNGGNAC NTGG                                      24
```

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:7:

```
CCNGGNGCNA RYTGNCKRAA YTGYTC                                    26
```

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:8:

ATAATGCCAG TCACCAAGTC T          21

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:9:

GATAGATTAA CTATTATACA TCGA          24

(2) INFORMATION FOR SEQ ID NO:10:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:10:

CCNGTNACNA ARWSNWSNWS NATHYTNATH ATHGGNGCNG GNACNTGGGG N          51

(2) INFORMATION FOR SEQ ID NO:11:

(i) SEQUENCE CHARACTERISTICS:
        (A) LENGTH: 48 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:11:

YTNACNMGNC CNGARCARTT YMGNCARYTN GCNCCNGGNG TNYTNAAR          48